US 11,241,211 B2

United States Patent
Qi et al.

(10) Patent No.: US 11,241,211 B2
(45) Date of Patent: Feb. 8, 2022

(54) METHOD AND APPARATUS FOR SINGLES SPECTRUM ESTIMATION AND FOR DEAD-TIME CORRECTION IN POSITRON EMISSION TOMOGRAPHY (PET)

(71) Applicant: CANON MEDICAL SYSTEMS CORPORATION, Otawara (JP)

(72) Inventors: Wenyuan Qi, Vernon Hills, IL (US); Yi Qiang, Vernon Hills, IL (US); Karthikayan Balakrishnan, Vernon Hills, IL (US); Yujie Lu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/816,953

(22) Filed: Mar. 12, 2020

(65) Prior Publication Data

US 2021/0282732 A1    Sep. 16, 2021

(51) Int. Cl.
*A61B 6/00* (2006.01)
*A61B 6/03* (2006.01)
(Continued)

(52) U.S. Cl.
CPC .......... *A61B 6/5235* (2013.01); *A61B 6/032* (2013.01); *A61B 6/037* (2013.01); *A61B 6/482* (2013.01); *A61B 6/5205* (2013.01); *A61B 6/5282* (2013.01); *G01T 1/2985* (2013.01); *G06T 11/005* (2013.01)

(58) Field of Classification Search
CPC ....... A61B 6/5235; A61B 6/032; A61B 6/037; A61B 6/482; A61B 6/5205; A61B 6/5282; G01T 1/2985; G06T 11/005
See application file for complete search history.

(56) References Cited

U.S. PATENT DOCUMENTS 5,350,925 A * 9/1994 Watson ............... G01V 5/12
250/264
6,008,493 A * 12/1999 Shao ................ G01T 1/1611
250/363.04

(Continued)

FOREIGN PATENT DOCUMENTS

WO    WO 2019/145398 A1    8/2019

OTHER PUBLICATIONS

John M. Ollinger. "Model-based scatter correction for fully 3D PET"; Phys. Med. Biol, Feb. 1996, pp. 153-176. http://www.researchgate.net/publication/14517016.

*Primary Examiner* — Blake C Riddick
(74) *Attorney, Agent, or Firm* — Oblon, McClelland, Maier & Neustadt, L.L.P.

(57) ABSTRACT

A method and apparatus is provided to perform dead-time correction in a positron emission tomography (PET) by estimating a full singles spectrum using a scatter model. The scatter model can use a Monte Carlo method, a radiation transfer equation method, an artificial neural network, or an analytical expression. The scatter model simulates scatter based on an emission image/map and an attenuation image/map to estimate Compton scattering. In the full singles spectrum, the singles counts with energies less than 511 keV are determined from the simulated scatter. The attenuation image can be generated based on X-ray computed tomography or based on applying a joint-estimation to PET data.

20 Claims, 14 Drawing Sheets

(51) Int. Cl.
*G01T 1/29* (2006.01)
*G06T 11/00* (2006.01)

(56) References Cited

U.S. PATENT DOCUMENTS

| | | | | |
|---|---|---|---|---|
| 6,410,920 | B1* | 6/2002 | Shao | G01T 1/1611 |
| | | | | 250/363.04 |
| 2004/0262520 | A1* | 12/2004 | Schotland | G06T 11/006 |
| | | | | 250/341.1 |
| 2005/0129170 | A1* | 6/2005 | Watson | G01T 7/005 |
| | | | | 378/5 |
| 2006/0091314 | A1* | 5/2006 | Williams | G01T 1/172 |
| | | | | 250/363.03 |
| 2010/0116994 | A1* | 5/2010 | Wollenweber | G01T 1/1611 |
| | | | | 250/363.03 |
| 2012/0290519 | A1* | 11/2012 | Fontaine | G01T 1/2985 |
| | | | | 706/20 |
| 2013/0303898 | A1* | 11/2013 | Kinahan | A61B 6/5264 |
| | | | | 600/425 |
| 2014/0314211 | A1* | 10/2014 | Zou | A61B 6/482 |
| | | | | 378/207 |
| 2014/0321604 | A1* | 10/2014 | Bourland | A61B 6/5205 |
| | | | | 378/7 |
| 2014/0365137 | A1* | 12/2014 | Burger | A61B 6/5217 |
| | | | | 702/19 |
| 2015/0379699 | A1* | 12/2015 | Takeuchi | H04N 5/23293 |
| | | | | 348/77 |
| 2017/0018099 | A1* | 1/2017 | Heukensfeldt | G06T 11/005 |
| 2017/0371046 | A1* | 12/2017 | Laurence | G01T 1/2985 |
| 2018/0353147 | A1* | 12/2018 | Wang | A61B 6/481 |
| 2019/0066341 | A1* | 2/2019 | Feng | A61B 6/037 |
| 2019/0066342 | A1* | 2/2019 | Zhu | G06T 11/005 |
| 2019/0251713 | A1* | 8/2019 | Chen | G06N 3/084 |
| 2020/0012002 | A1* | 1/2020 | Kobayashi | G06T 11/005 |
| 2020/0015744 | A1* | 1/2020 | Fang | A61B 5/14553 |
| 2020/0170605 | A1* | 6/2020 | Qi | G01T 1/2985 |
| 2020/0170607 | A1* | 6/2020 | Yu | A61B 6/06 |
| 2020/0233099 | A1* | 7/2020 | Adler | G01T 1/40 |
| 2020/0268252 | A1* | 8/2020 | Litvinova | G01J 3/14 |
| 2020/0363542 | A1* | 11/2020 | Song | G01T 1/171 |
| 2021/0030387 | A1* | 2/2021 | Andreyev | G16H 30/20 |

* cited by examiner

METHOD AND APPARATUS FOR SINGLES SPECTRUM ESTIMATION AND FOR DEAD-TIME CORRECTION IN POSITRON EMISSION TOMOGRAPHY (PET)

FIELD

The illustrative embodiments described herein relate to estimating a full singles spectrum from radiation measurements representing energy-window filtered counts, and, more particularly, to using the estimated singles spectrum to perform a dead-time correction of the measured radiation.

BACKGROUND

Positron emission tomography (PET) is an imaging method in nuclear medicine based on the use of a weak radioactively marked pharmaceutical (a tracer) to image certain features of a body. PET images display the spatial distribution of the radiopharmaceutical enabling a doctor or clinician to draw conclusions about metabolic activities or blood flow, for example.

In PET imaging, a tracer agent is introduced into the patient to be imaged (e.g., via injection, inhalation, or ingestion). After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

During this process, a tracer attached to the agent will emit positrons, which is the anti-matter equivalent of the electron. When an emitted positron collides with an electron, the electron and positron are annihilated, resulting in the emission of a pair of gamma rays each having an energy of 511 keV and the two gamma rays traveling at substantially 180 degrees apart.

The spatio-temporal distribution of the tracer is reconstructed via tomographic reconstruction principles, e.g., by characterizing each detection event for its energy (i.e., amount of light generated), its location, and its timing. When two gamma rays are detected within a coincidence time window, they likely originate from the same positron annihilation event, and, therefore, are identified as being a coincidence pair. Drawing a line between their locations, i.e., the line-of-response (LOR), one can determine the likely location of the positron annihilation event. The timing information can also be used to determine a statistical distribution along the LOR for the annihilation based on a time-of-flight (TOF) information of the two gamma rays. By accumulating a large number of LORs, tomographic reconstruction can be performed to determine a volumetric image of the spatial distribution of radioactivity (e.g., tracer density) within the patient.

Due to the dead-time of the detector, some counts will not be recorded. For example, after detecting a quanta of radiation (e.g., an X-ray or a gamma ray), the detector can experience a dead time during which no detections will occur. Improved image quality can b achieved by accounting for and correcting the acquired data for missed counts arriving during the dead time. This dead-time correction depends on how accurately the flux rate can be determined. The accuracy of the flux rate is limited in PET scanners that filter out scatted events by filtering out counts outside of an energy window because the measured flux rate fails to account for flux across the whole singles spectrum.

Accordingly, improved methods for dead-time correction are desired in order to estimate the complete singles spectrum from a windowed portion of the radiation spectrum.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

SUMMARY

Figure 1A:
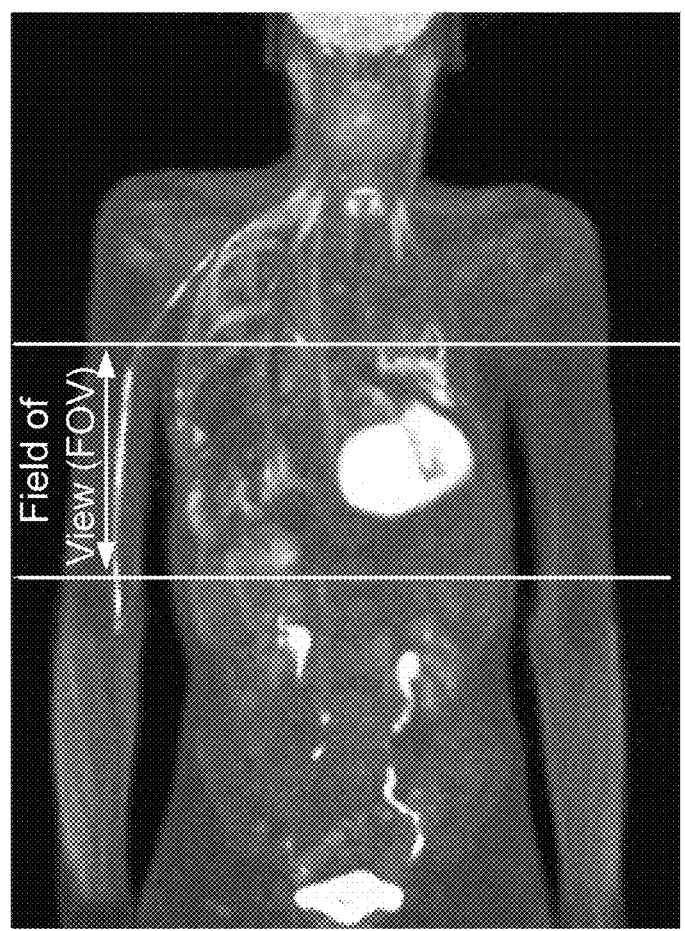
FIG. 1A shows a positron emission tomography (PET) image of a smaller patient, according to one implementation.

According to aspects of one embodiment, there is provided an apparatus that includes circuitry. The circuitry is configured to (i) obtain radiation data representing an intensity of radiation detected at a plurality of detector elements, the radiation data comprising counts that have been filtered using an energy band-pass filter to generate filtered data, an energy range of the energy band-pass filter including an energy of the radiation when the radiation is not scattered; (ii) estimate, based on the radiation data, a singles spectrum of the radiation detected at a plurality of detector elements, the singles spectrum being estimated using a scatter model; and (iii) perform a dead-time correction correct on the radiation data based on the estimated singles spectrum, correcting the radiation data for missed detections arising from a dead time of respective detector elements of the plurality of detector elements to generate corrected radiation data.

According to aspects of another embodiment, there is provided a method of (i) obtaining radiation data representing an intensity of radiation detected at a plurality of detector elements, the radiation data comprising counts that have been filtered using an energy band-pass filter to generate filtered data, an energy range of the energy band-pass filter including an energy of the radiation when the radiation is not scattered; (ii) estimating, based on the radiation data, a singles spectrum of the radiation detected at a plurality of detector elements, the singles spectrum being estimated using a scatter model; and (iii) performing a dead-time correction correct on the radiation data based on the estimated singles spectrum, correcting the radiation data for missed detections arising from a dead time of respective detector elements of the plurality of detector elements to generate corrected radiation data.

DETAILED DESCRIPTION

In positron emission tomography (PET), gamma rays are detected, e.g., by a combination of scintillator crystals together with a photodetectors, such as photomultiplier tubes (PMTs) or silicon photomultipliers (SiPMs). After detecting a gamma ray, these photodetectors can undergo a dead-time period before the detector recovers and is able to detect another gamma ray. During this dead time, a gamma ray incident on the detector will not be detected, resulting in a missed count. The number of missed can be determined based on the incident flux rate, the dead time, and the photon statistics (e.g., Poison statistics). Accordingly, by estimating the total flux (e.g., the full singles spectrum), the measured counts can be corrected for dead-time loss, thereby improving accuracy and image quality.

To remove the scattered events in PET, a narrow energy window is often selected for the detected counts. In previous methods the dead-time estimation was based on the measured counts, which omits counts outside of the energy window. These previous methods underestimate the dead-time because they fail to account for gamma rays outside the energy window, which also contribute the dead-time loss. Therefore, if the outside energy window count rate could be estimated, it would be helpful for more accurate dead-time loss estimation and correction. That is, a method that accounts for counts both outside and inside the energy window will lead to more accurate PET reconstruction scaling, which is important for clinical diagnose and treatment monitoring.

As discussed above, dead time will occur regardless of whether the gamma ray has an energy of 511 keV (i.e., a direct gamma ray from a positron emission event) or is a scattered gamma ray (e.g., resulting from Compton scattering of a direct gamma ray). In PET scanners, the measured singles counts are selected to be within an energy window that spans the 511 keV peak for positron emission. As mentioned above, using only the counts within the energy window to perform a dead-time correction would underestimate the total flux (i.e., the gamma-ray flux due to both direct/primary gamma rays and scattered gamma rays), and therefore underestimate the dead-time loss. Moreover, the ratio between primary and scatter flux can vary from patient to patient because gamma rays passing through a larger patient pass through more mater increasing the likelihood that the gamma rays will be scattered.

Moreover, in PET, the measured coincidences include both true coincidences and a background signal (e.g., random coincidences). The background signal includes counts due to random events and scatter events. In PET, the background signal is primarily made up of accidental coincidences (ACs), also known as randoms, and scatters.

For many annihilation events, only one photon of a pair of photons is detected because the other photon is absorbed or scattered out of plane of a PET detector ring. Further, some photon reaching the scintillating detectors of the PET detector ring are not detected due to a less than unity quantum efficiency of the detectors. Detection events in which one of a pair of photons is detected can be referred to as "singles." This includes the case where only one of the pair of photons is detected, and the case that both of the pair of photons are detected. If two singles from separate annihilations are detected within the coincidence timing window, then they are mistakenly registered as having arisen from the same annihilation. This is called an accidental coincidence (AC) event, also known as a random event. Stated differently, an AC event occurs when two unrelated singles are detected within a coincidence timing window. When an AC even has a line of response (LOR) passing outside of the object OBJ being imaged, the detection is said to be in the "wings."

Although most scattered photons in the body leave the detector plane undetected, some scattered photons are still detected and registered resulting in an incorrect LOR. In certain implementations, some of these scattered events resulting in incorrect LORs can be removed by energy discrimination because photons lose a fraction of their energy during the Compton interaction giving rise to the scatter event. Even so, some scattered photons (scatters) and some random coincidences (randoms) will inevitable be recorded, and, thus, the background signal includes the randoms and the scatters.

Singles are not limited to ACs, but can include randoms and scatters that do not occur within the time window of another gamma ray and are thus not recorded as being part of a coincident pair of gamma rays. All gamma rays that are detected whether or not they are true coincidences, ACs, or randoms and scatters that are not recorded as coincidences (i.e., all singles) will cause the detector to undergo a dead-time period during which the detector does not detect gamma rays, resulting in missed counts. The accuracy of a dead-time correction depends on how accurately the total missed counts can be estimated. This entails determining all the singles giving rise to the dead time. In addition to the above time window that is applied to remove ACs, an energy window is also applied to remove scatters, which have energies that are less than 511 keV, which is indicative of positron emission in the absence of scattering. Because singles of all energies result in the dead-time detector response, it is preferred to account for the full spectrum of singles counts in the dead-time correction.

The methods described herein estimate of the full singles spectrum for gamma rays based on an emission image and an attenuation image of the patient. This full singles spectrum can then be used to better correct for dead-time loss.

Figure 1B:
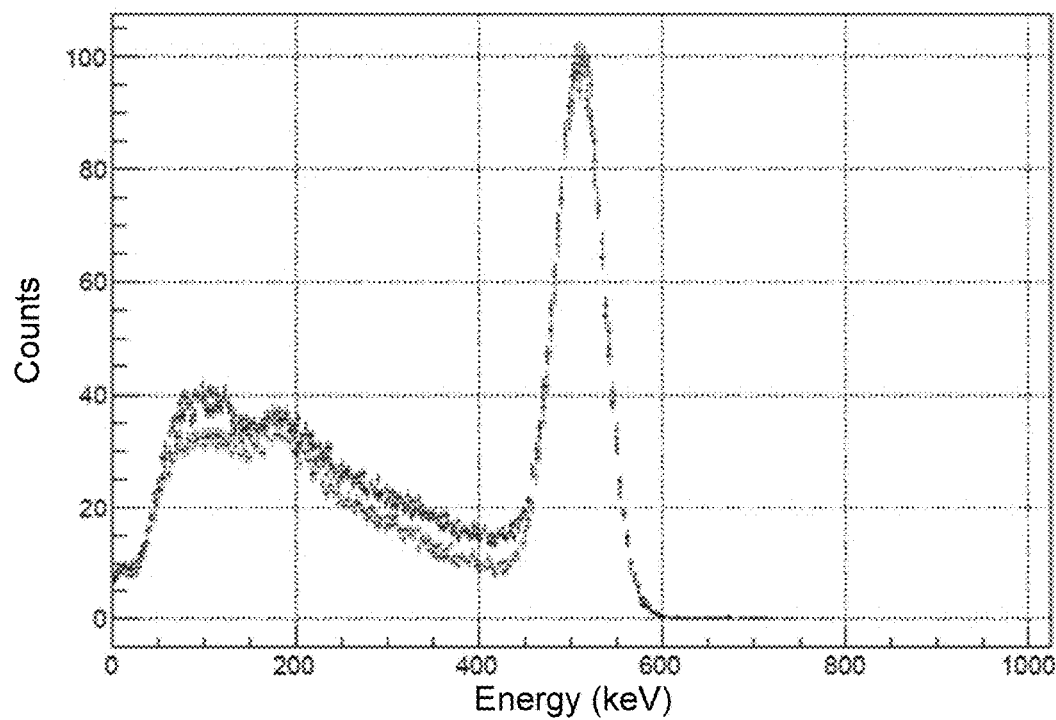
FIG. 1B shows an energy spectrum of gamma rays acquired for the field of view (FOV) shown in FIG. 1A, according to one implementation.

Referring now to the drawings, wherein like reference numerals designate identical or corresponding parts throughout the several views, FIG. 1A shows a PET image of a smaller patient, and FIG. 1B shows the singles count spectrum for the smaller patient. The singles count spectrum represents the singles counts as a function of energy. In the singles count spectrum, a peak is centered at the 511 keV for positron emission, but a larger number of gamma rays are at lower energies due to inelastic scattering (e.g., Compton scattering). In a PET scan, an energy window is often applied to selectively record the counts around the 511 keV peak. However, knowledge of the full singles spectrum can improve dead-time corrections for PET imaging. Accordingly, the methods described herein estimate the full singles spectrum from energy-windowed, measured counts.

Figure 2A:
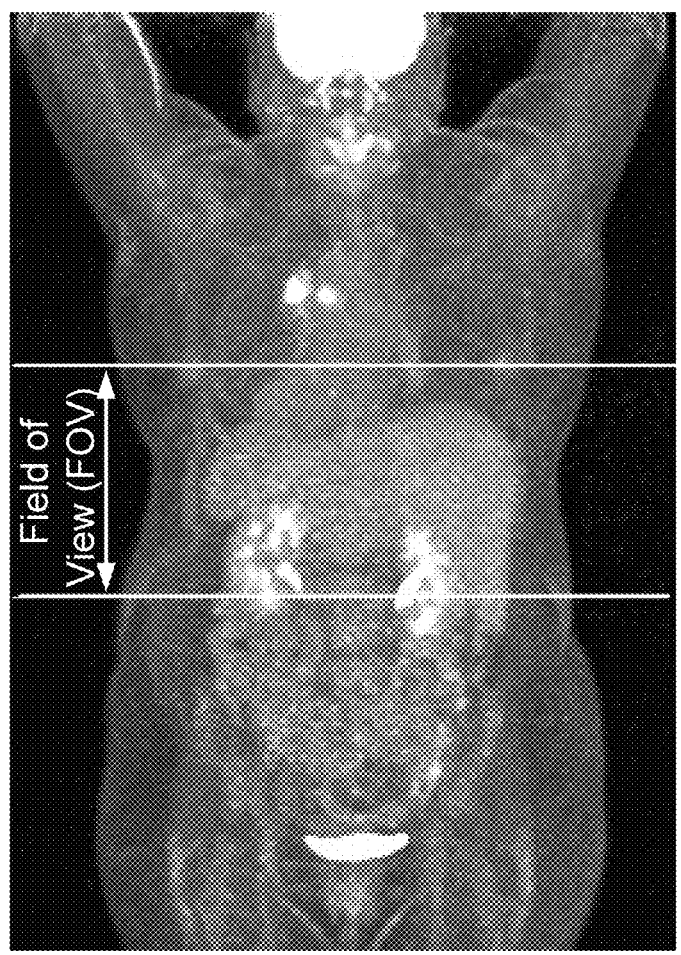
FIG. 2A shows a PET image of a larger patient, according to one implementation.
Figure 2B:
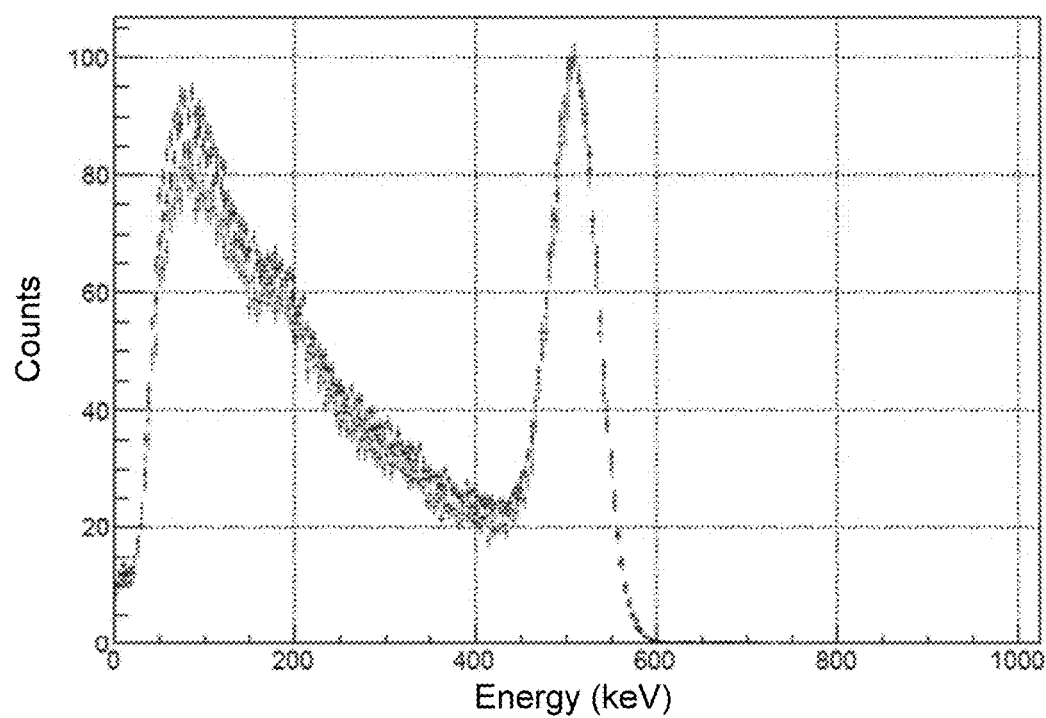
FIG. 2B shows an energy spectrum of gamma rays acquired for the FOV patient shown in FIG. 2A, according to one implementation.

Similar to FIGS. 1A and 1B, FIG. 2A shows a PET image of a larger patient, and FIG. 2B shows the singles count spectrum for the larger patient. A comparison of FIG. 1B with FIG. 2B shows that the larger patient increases the percentage of scattered gamma rays. Further, in the case shown in FIG. 2A a larger percentage of the emission density occurs outside of the imaged FOV. As can be observed, various factors contribute to the relative number of gamma ray counts corresponding to energies within and without a given energy window. A method that models these various factors to estimate the full singles spectrum and provides the ratio of counts within and without the energy window would improve the accuracy of the correction due to dead-time loss, resulting in improved accuracy and better image quality for the PET image.

In FIGS. 1A and 2A, the images are knitted together from a series of single scans each corresponding to the single-scan width (i.e., the width of the single-bed-scan FOV) shown in FIGS. 1A and 2A.

Figure 3A:
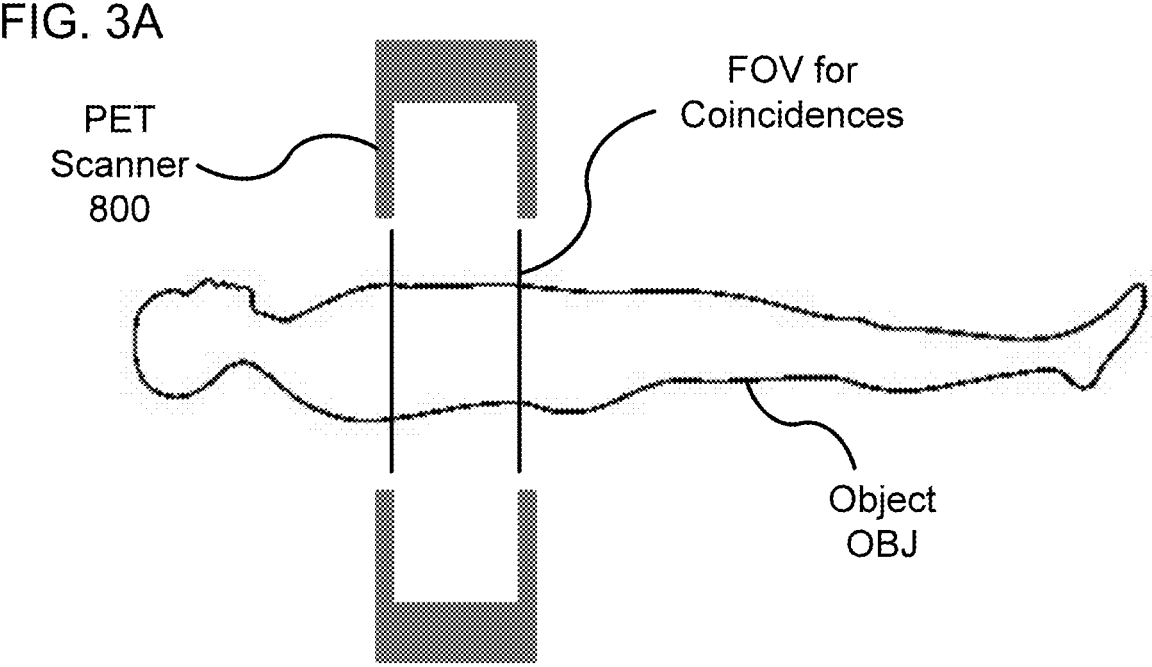
FIG. 3A shows a diagram for a FOV of true coincidences in a PET scanner, according to one implementation.

FIG. 3A shows a PET scanner 800 in relation to an object OBJ that is being imaged. FIG. 3A also shows the imaging FOV (i.e., the FOV for true coincidences) in which both gamma rays arrive at the detectors without undergoing scatter. For example, the FOV in FIG. 3A can be for true coincidences when a PET scanner 800 is performing a single-bed scan.

Figure 3B:
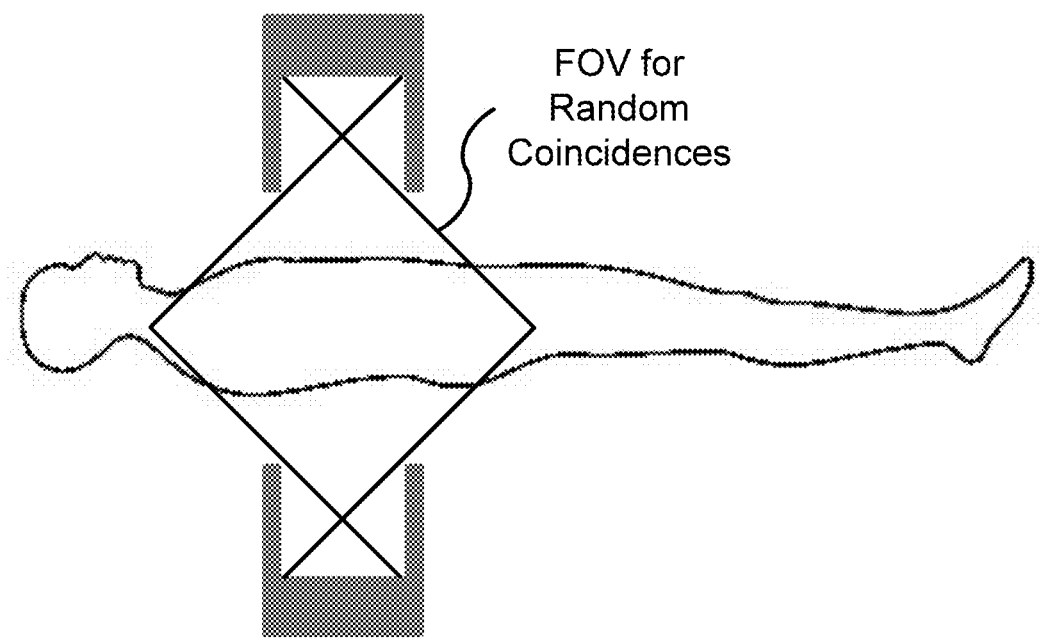
FIG. 3B shows a diagram for a FOV of random coincidences in the PET scanner, according to one implementation.

FIG. 3B shows a schematic diagram of the region in which gamma rays can originate giving rise to random coincidences. Thus, random coincidences can arise from regions outside of the imaging FOV (i.e., the FOV for true coincidences shown in FIG. 3A). Because singles include scatters in addition to randoms (i.e., random coincidences), the singles can include gamma rays for which the scattering event occurs within the randoms FOV and the gamma-ray emission occurs either in or out the randoms FOV. That is, the singles spectrum corresponding to scattered gamma rays can arise from gamma rays originating/emitted both inside and outside the FOV for random coincidences, so long as the scattering event lies within the FOV for random coincidences.

In two-dimensional (2D) and/or three-dimensional (3D) PET, the scatter effect is one of the most significant physical factors degrading the image quality. In a typical 3D PET system, scatter events can be between 30% and 50% of total detected events. Model based scatter estimation can provide an accurate estimate of the scatter. When the object is longer in and axially direction than the PET scanner, outside-the-FOV scatter (i.e. scattered gamma rays coming from outside the imaging FOV) should preferably be accounted for. Such outside-the-FOV scatter can exceed 40% of total scatter, especially when the PET system has a big bore opening without end shielding. Like the general scatter discussed above, outside-the-FOV scatter events can be viewed in two categories: (i) events that originate within the FOV where one or both of the detected photons scatter from matter located outside of the FOV and (ii) events that originate from annihilation events (i.e., activity) occurring outside of the FOV. For both categories, attenuation and activity distributions outside-the-FOV can be used to model the detected scatter distribution.

To better understand the methods described herein, a distinction between coincidence counts and single counts should be understood. For PET image reconstructions, it is the coincidence counts that are important because these determine the line of response (LOR) for positron emission events. However, for dead-time correction, it is the singles counts that are important because every count regardless of whether it is a coincidence or not will result in dead time for the detector. Accordingly, it should be understood that when the context of the discussion herein is directed to PET image reconstruction the relevant gamma-ray detection events are coincidences, and understood that when the context of the discussion herein is directed to dead-time correction, e.g., the relevant gamma-ray detection events are singles.

In the context of PET image reconstruction, for a gamma ray that scatters into the FOV from the outside of the FOV, two conditions are often imposed for a gamma ray to be detected and then recorded. First, the event has to scatter at such an angle that it hits a detector surface. Second, after the scatter, the gamma ray has to have an energy within the energy window. In view of these two detection conditions, the majority of the outside-the-FOV events come from the immediately adjacent bed positions because the probability of scatter (i.e., the scatter cross-section) is greater for smaller scatter angles and because scattered events originating in the immediately adjacent bed position can scatter at larger angles and still be detected.

Figure 4A:
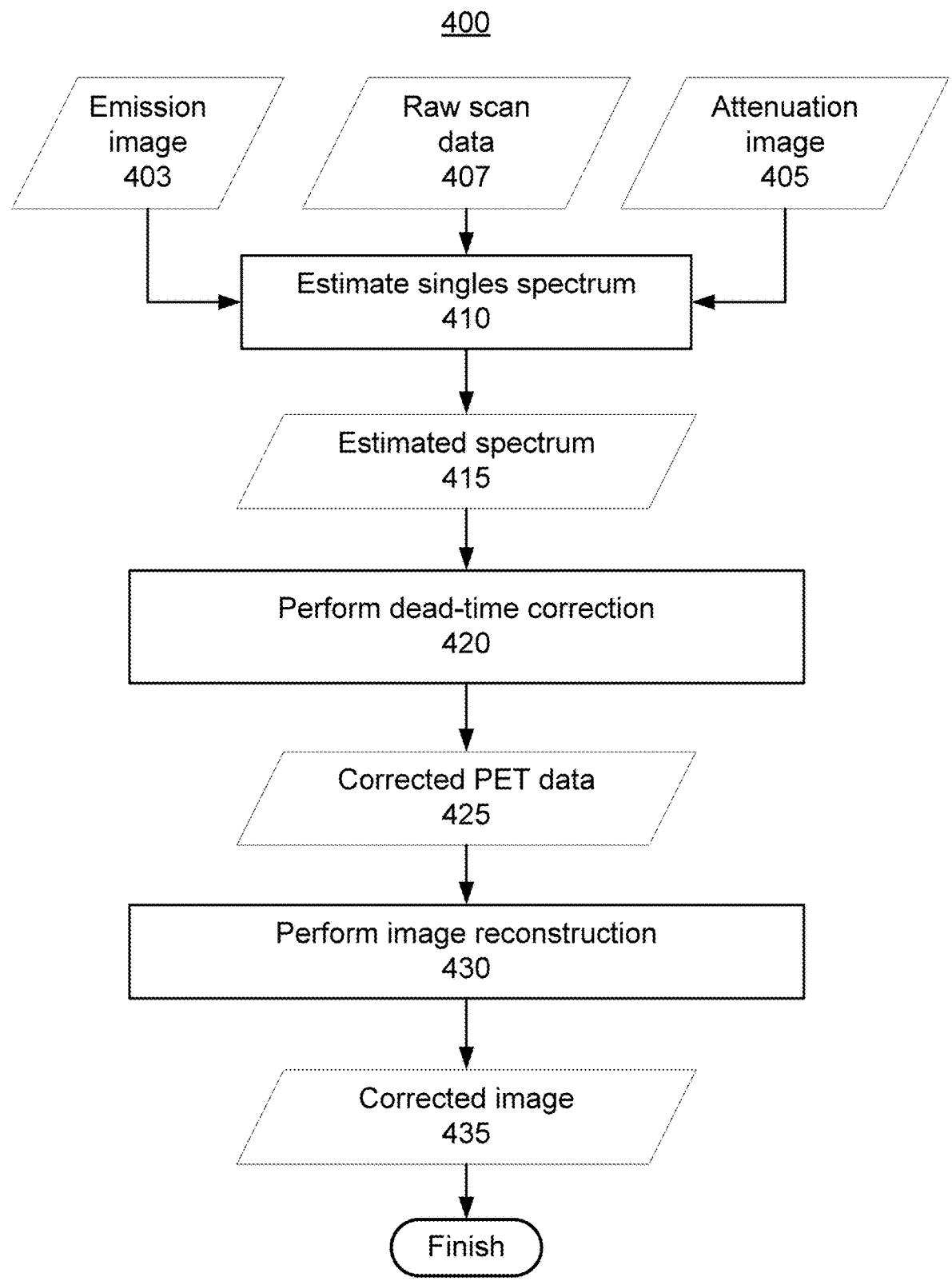
FIG. 4A shows a flow diagram of a method for estimating a full singles spectrum from energy filtered counts, and then performing dead-time correction followed by image reconstruction, according to one implementation.
Figure 4B:
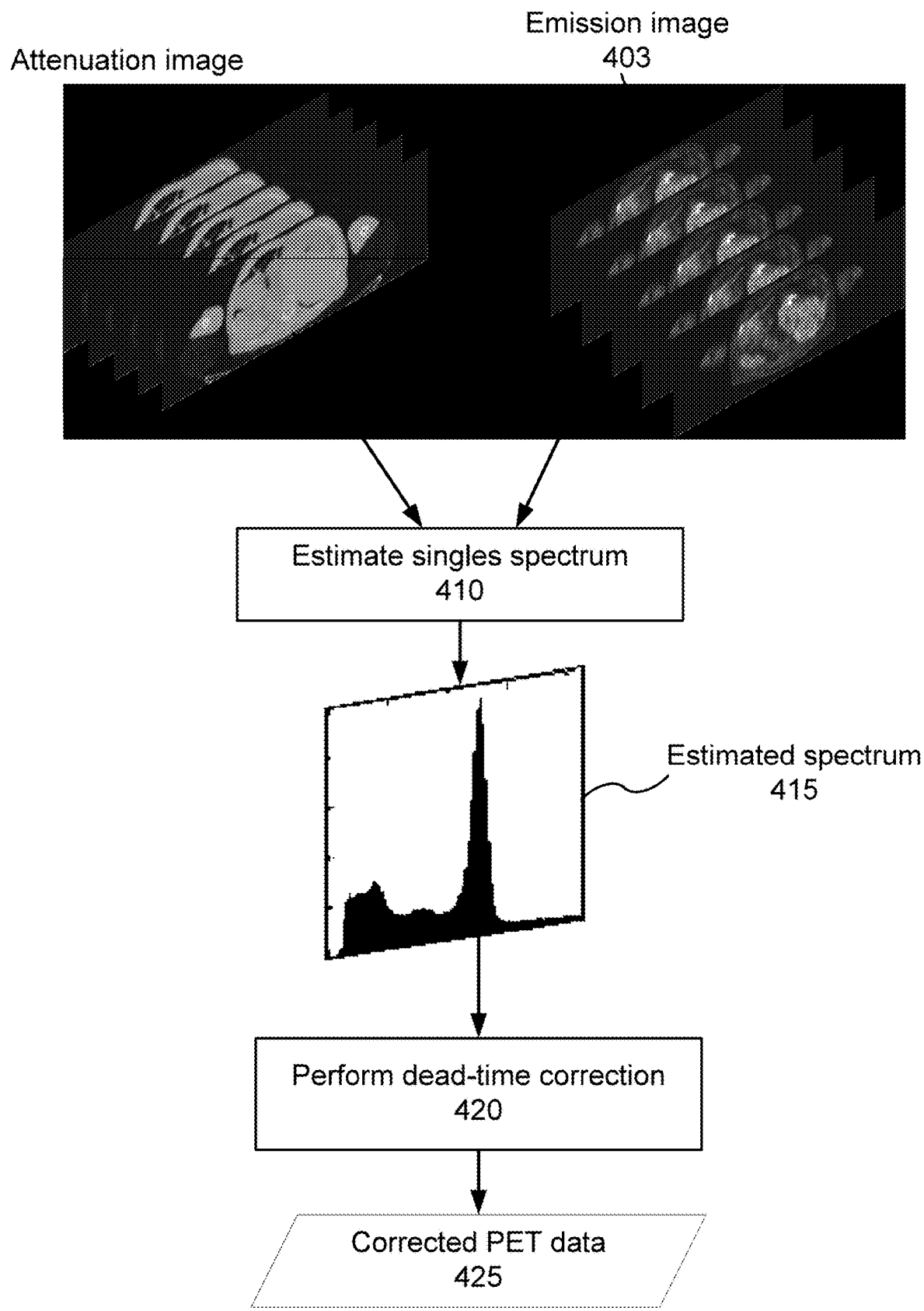
FIG. 4B shows a flow diagram of the a full singles spectrum estimation method that uses attenuation and emission images to estimate the full singles spectrum and then perform dead-time correction, according to one implementation.

In view of the energy window applied to filter out scatter, the acquired counts in a PET scan do not include detections for scattered gamma rays having energies below the energy window. These counts of lower-energy gamma rays nevertheless contribute to the dead time, and to be as accurate as possible a dead-time correction should account for missed counts due to the dead time arising from the low-energy gamma rays. Accordingly, FIGS. 4A and 4B illustrate flow diagrams of a method 400 for estimating a full spectrum of singles counts from the acquired counts (e.g., counts that have been filtered to fall within an energy window). The estimated spectrum 415 is then used to perform a dead-time correction of the raw data 407, and then reconstruct an image 435 from the corrected data 425.

In step 410, the singles spectrum 415 is estimated from the emission image 403 and the attenuation image 405. FIG. 4A shows that the raw PET data 407 can optionally be an input to step 410. In certain implementations, the raw PET data 407 can be used to generate the emission image 403 and the attenuation image 405.

For example, a joint-estimation method can be used to simultaneously derive both the attenuation image 405 (also referred to as an attenuation map) and the emission image 403 (also referred to as an emission map or as an activity distribution). When a joint-estimation method is used, both the attenuation image 405 and the emission image 403 can be generated from the raw PET data 407.

In other implementations, the raw data 407 can be acquired using a PET/CT scanner that scans the object OBJ being imaged to generate both PET data and X-ray computed tomography (CT) data. The PET data can be used to generate the emission image 403 and the X-ray CT data can be used to generate the attenuation image 405. Additional approaches can also be used to generate the emission image 403 and the attenuation image 405. For example, the emission image 403 can be generated from the PET data 407, and the attenuation image 405 can be generated using a body atlas. The attenuation image 405 is used to estimate the scatter cross-sections as a function of position within the imaged object OBJ.

Various methods can be used to estimate a singles spectrum 415 from the attenuation image 405 and the emission image 403. In each of these various methods, the attenuation image 405 can be used to generate a scatter-cross-section model (e.g., the gamma-ray scatter cross-section as a function of position). Different materials, such as bone and water, have different scattering cross-sections with different angular dependences depending on their atomic constituents. Also, the magnitude of the scatter cross-section can depend on the density of material components at a given point. Accordingly, in certain implementations, the attenuation image 405 can be decomposed into material components using a material decomposition to determine the density of various material components as a function of position.

For example, voxels with Hounsfield values above a given threshold can be determined to be bone, whereas voxels with Hounsfield values below another threshold can be identified as soft tissues. Then a threshold-and-region-growing method can be used to partition the attenuation image 405 into material components. Further, when spectral CT is used to generate the attenuation image 405, material decomposition can be used to determine the position-dependent scatter cross-section. Further, a body atlas and/or machine learning methods can be used to determine the position-dependent scatter cross-section from the attenuation image 405, as well as other method as would be understood as a person of ordinary skill in the art.

Thus, in certain implementations, a position-dependent scatter cross-section can be obtained from the attenuation image 405 and from material components derived therefrom. The position-dependent X-ray scatter cross-section can be obtained as a linear superposition of respective products between the volume pixel (i.e., voxel) density ratios of the material components of the material decomposition and pre-calculated scatter cross-sections corresponding to the respective material components.

Returning to the various methods used to estimate the singles spectrum 415 from the attenuation image 405 and the emission image 403, in one implementation, a neural network can be trained to estimate the singles spectrum 415 in response to inputs of the emission image 403 and the attenuation image 405. In another implementation, a Monte Carlo (MC) method can be used to estimate the scatter based on the emission image 403 and the attenuation image 405. In a third implementation, a radiative transfer equation (RTE) method can be used to estimate the scatter based on the emission image 403 and the attenuation image 405. A fourth alternative is to use an analytical calculation to estimate the scatter 415. Each of these alternatives are discussed below in greater detail.

In step 420, the singles spectrum 415 is used to perform dead-time correction on PET data. The dead time of a gamma detector can depend on the flux and energy spectrum of incident gammas:

$$\text{dead time} = \int_0^\infty \tau(E) p(E) dE$$

wherein E is the photon energy, $\tau(E)$ is the dead time induced by a single photon with energy E, and $p(E)$ is the incident flux distribution as a function of energy E. If the dead time is a constant, rather than being dependent on the gamma-ray energy, the above expression simplifies to $$\text{dead time} = \tau \int_0^\infty p(E) dE = \tau N_{Total},$$

wherein $$N_{Total} = \int_0^\infty p(E) dE$$

is the count rate. In practice, the measured counts include only a narrow window [E1 E2], wherein E1<511 keV<E2. That is, the PET scanner acquires an incident flux integrated within a narrow window [E1, E2]. Nevertheless, the measured count rate $$N_{meas} = \int_{E1}^{E2} p(E) dE$$

can be used to calculate the dead time by scaling the dead time per count $\tau$ to an effective dead time per count $\tau_c$, which is the dead time per measured count $N_{meas}$, and is calculated as $$\tau_c = \tau \frac{\int_0^\infty p_c(E) dE}{\int_{E1}^{E2} p_c(E) dE},$$

wherein $p_c(E)$ is the flux distribution during a dead-time calibration. If the ratio between the total counts $N_{Total}$ to the measured counts $N_{meas}$ where patient independent, then the dead time for a given flux rate $p_0(E)$ during a PET scan could be calculated as $$\text{dead time}' = \tau_c \int_{E1}^{E2} p_0(E) dE.$$

However, FIGS. 1B and 2B show that show that the spectral shape of the flux rate $p_o(E)$ can vary between patients of different sizes and can depend on the distribution of emission density inside and outside of the FOV. Thus, a better approach is to estimate an energy dependent flux rate $p_{est}(E|N_{meas})$ from the measured counts $N_{meas}$, as described in step 410. Then, the estimated full singles spectrum (i.e., the estimated flux rate $p_{est}(E|N_{meas})$) can be used to determine the dead time using the expression $$\text{dead time}' = \tau \int_0^\infty p_{est}(E|N_{meas}) dE.$$

Once the dead time has been estimated, Poison statistics can be used to determine the correction factor that is applied to the raw data 407 to generate the corrected PET data 425.

In step 430, a PET image is reconstructed from the corrected PET data 425. In PET, the emission data can be configured as a sinogram (similar to projection data in X-ray CT), and, therefore, methods similar to those applied in X-ray CT to reconstruct attenuation images can be applied to reconstruct activity images representing the activity/tracer density as a function of position/voxel index. These reconstruction methods include, e.g., filtered back-projection (FBP) methods and iterative reconstruction (IR) methods.

In certain implementations using IR reconstruction, the reconstructed image ¥ is generated by solving the optimization problem $$\hat{x}(y) = \underset{x \geq 0}{\operatorname{argmax}}[L(y \mid x) - \beta \phi(x)],$$

wherein y is the measured sinogram, x is the unknown radioactive tracer/activity distribution, $L(y|x)$ is the log likelihood function, $\phi(x)$ is the regularizer (also referred to as a regularization function or penalty function), and $\beta$ is the regularization parameter that controls the degree of regularization (also referred to as a penalty strength). In the above objective function, $L(y|x)$ is the data-fidelity term and $\phi(x)$ is the regularization term (also known as regularizer). The regularization parameter $\beta$ provides the relative weight between the data-fidelity regularization and terms. For example, when the regularization term penalizes variations/noise in the reconstructed PET image, increasing the value of the regularization parameter $\beta$ increases the degree of smoothing with corresponding reductions to both the noise level and the spatial resolution.

In certain implementations, the regularizer can be a patch-based edge-preserving penalty function, which uses neighboring patches instead of individual pixels to compute the penalty as exemplified by the expression $$\phi(x) = \sum_{j=1}^{N} \sum_{l \in N_j} \gamma_{jl} \psi(|f_j(x) - f_l(x)|),$$

wherein the $\ell$-2 norm or Euclidean distance, which is given by $$|f_j(x) - f_l(x)| = \sqrt{\sum_{k=1}^{n_k} (x_{jk} - x_{lk})^{\wedge}2}$$

can be used the measure of distance between the patches of pixels surrounding pixel j and pixel l, $N_j = \{x_{j1}, x_{j2}, \ldots, x_{1jk}\}$ denotes the neighborhood of pixel j, $\gamma_{jl}$ is the weight related to the distance between pixel j and pixel l, and $\psi(\bullet)$ is the potential function. The regularizer discussed above is straightforward to generalize and can be applied for both pairwise and patch-based penalties, as would be understood by a person of ordinary skill in the art. Other regularizers can be used without departing from the spirit of the methods described herein, as would be understood by a person of ordinary skill in the art.

Returning to step 410, details are now provided regarding the four types of methods for estimating the full singles spectrum: (i) Monte Carlo (MC) simulation; (ii) analytical calculation; (iii) radiative transfer equation (RTE) method, (iv) machine learning method.

First, the full singles spectrum 415 can be generated using a MC simulation method, such as the Geant4 Application for Tomographic Emission (GATE) tool kit, as discussed in S. Jan et al., "GATE-Geant4 Application for Tomographic Emission: a simulation toolkit for PET and SPECT," Phys Med Biol. Vol. 49, pp. 4543-4561 (2004), which is incorporated herein by reference in its entirety. MC simulation can be computationally intensive and slow in order to perform a sufficiently large number of simulations to overcome the inherent noise in the MC simulation, but MC simulation has offsetting advantages. For example, MC simulation can be accurate, and the simulation results can provide the ground truth, which is important for evaluating the system and validating some of the other algorithms discussed below. Further, some hidden variables in real acquisition can be directly measured in Monte Carlo simulation, like scatter and randoms. Using the reconstructed emission map 403 and attenuation map 405, MC simulation directly generates the singles spectrum corresponding to a PET acquisition.

Figure 5:
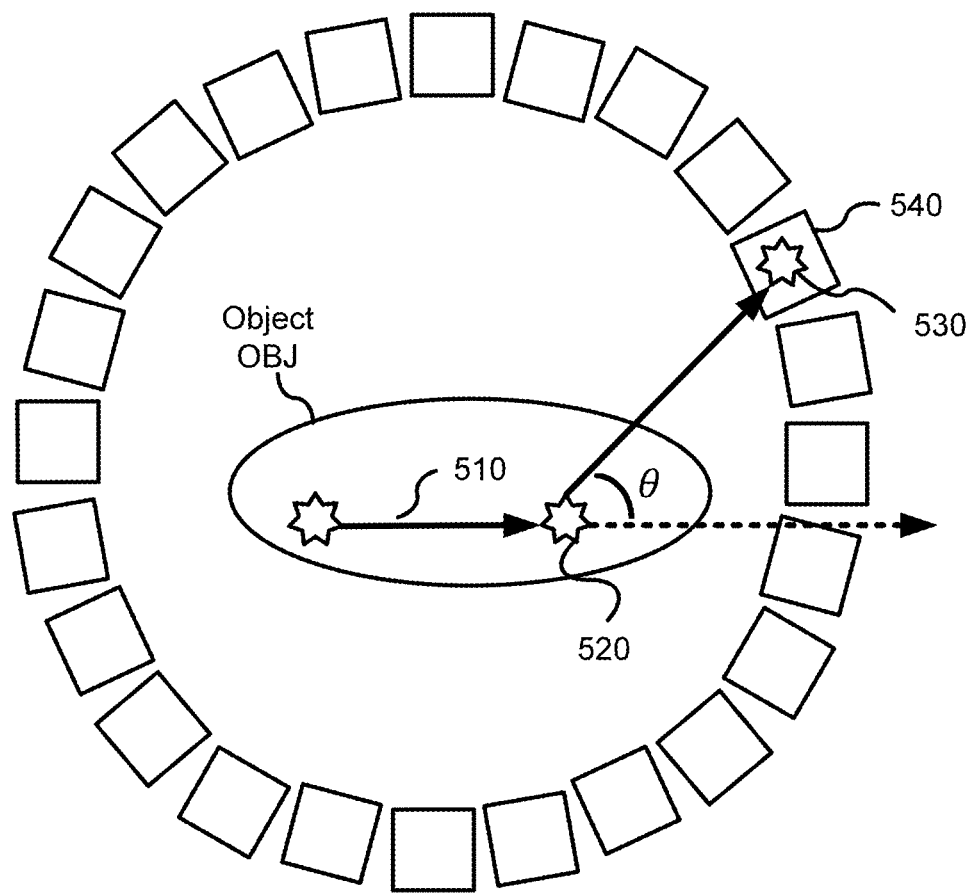
FIG. 5 shows a schematic diagram of scatter in a PET scanner, according to one implementation.

Second, the full singles spectrum 415 can be generated using an analytical calculation, as discussed in C. C. Watson, "New, faster, image-based scatter correction for 3D PET," IEEE Trans. Nucl. Sci., vol. 47, no. 4, pp. 1587-1594, (2000), which is incorporated herein by reference in its entirety. FIG. 5 shows first-order scatter within a PET scanner 800. For example, the first order scatter calculated using the expression $$\text{Scat} = \int_{V_S} dV_S \left( \frac{\sigma_{SD}}{4\pi R_{SD}^2} \right) \frac{\mu}{\sigma_c} \frac{d\sigma_c}{d\Omega} \int_{V_f} f dV_f \int_S^D \mu ds \int_S^A \mu ds,$$

wherein $$\frac{d\sigma_C}{d\Omega} = \frac{r_0^2}{2} \left( \frac{1}{2 - \cos\theta} \right)^2 \left[ 1 + \cos^2\theta + \frac{(1 - \cos\theta)^2}{2 - \cos\theta} \right],$$

$S(V_S)$ is the scatter point 520 as a function of the scatter volume $V_S$, "A" denotes the annihilation point 510, "D" denotes a detection point 530 within the detector 540, $\sigma_c(d\sigma_c)$ is the total Compton cross section, i.e. the scatter cross section, as a function of the differential Compton cross section, $\sigma_{SD}$ is the detector cross section normally to the ray from the scatter point 520 to the detection point 530, $f(V_f)$ is the emission density as a function of the emission volume $V_f$, $R_{SD}$ is the distance from the scatter point 520 to the detection point 530, $r_0$ is the classical electron radius (i.e., 2.818×10-15 m), and $\mu$ is the linear attenuation coefficient. This method of calculating the scatter can be referred to as either the analytical method or as the first scatter estimation algorithm.

Figure 6A:
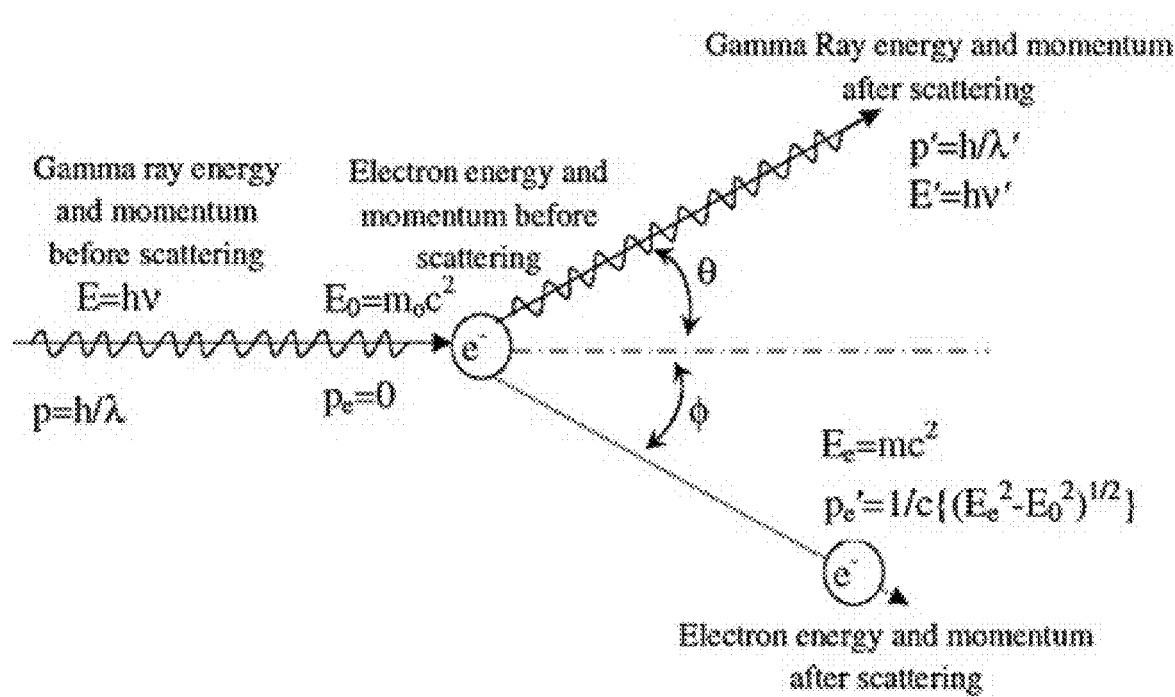
FIG. 6A shows a schematic diagram of Compton scatter, according to one implementation.
Figure 6B:
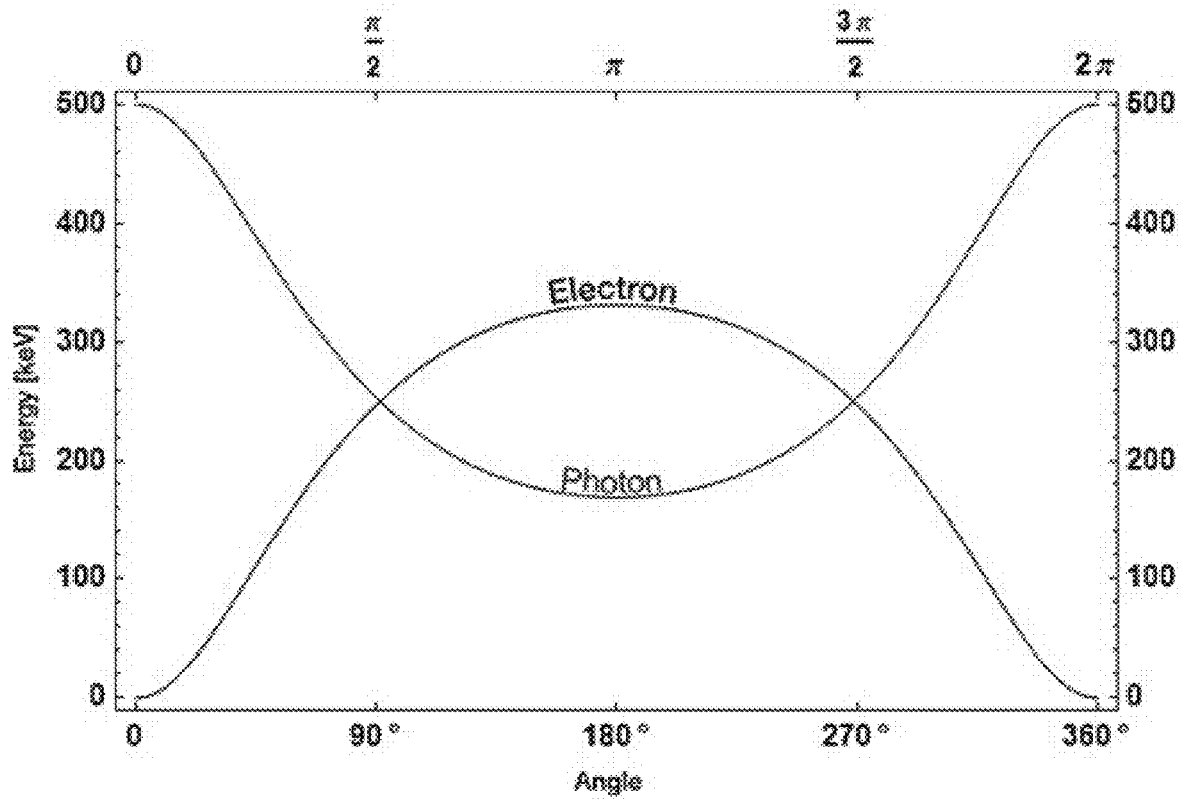
FIG. 6B shows, for Compton scattering, a plot of the electron and photon energies as a function of angle, according to one implementation.

FIG. 6A shows, for Compton scattering, the relation between the energy and momentum of the incoming gamma ray, the outgoing gamma ray, and the scattered electron. The angles $\phi$ and $\theta$ are determined by the fact that the scatter conforms to the laws of conservation of energy and momentum. The energy of the scattered electron is the energy deposited in the first crystal. Further, the remaining energy is carried away by the outgoing gamma ray. Consequently, when there is only a single scattering event, the energy of outgoing gamma ray is deposited in a second crystal by converting, via photoelectric absorption, the energy of the outgoing gamma ray by in to secondary photons, (e.g., with wavelengths in the optical, ultra-violate, and infrared spectra). In general, these energies are related by the "Compton shift," which is that the difference between the wavelengths of the outgoing and incoming gamma rays, which is given by $$\lambda' - \lambda = h/(m\ c)(1 - \cos\theta),$$

wherein $\lambda$ is the initial wavelength, $\lambda'$ is the wavelength after scattering, h is the Planck constant, m is the electron rest mass, c is the speed of light, and $\theta$ is the scattering angle of the gamma ray. The energy is inversely related to the wavelength by the Planck constant h, i.e., $E=h/\lambda$. FIG. 6B shows that relation between the scattered photon energy and the electron energy as a function of the scatter angle, assuming the initial gamma ray photon energy is 511 keV.

In view of the above, the scattered photon's energy E' is given by:

$$E' = \frac{E}{1 + \frac{E}{m_e c^2}(1 - \cos\theta)}$$

When the incoming photon's energy is fixed at 511 keV, the above equation is simplified to:

$$E' = \frac{511}{2 - \cos\theta}$$

According to previous calculations, the first-order scatter singles can be calculated for the full energy spectrum. The first-order scatter can reasonable approximate all orders of scatter by multiplying the first-order scatter by a scale factor. The scale factor can be determined using the wings in the raw data 407. For example, scatter will give rise to LORs that do not pass through or overlap with the object OBJ being imaged, which are referred to as wings. By scaling the first-order scatter such that it agrees with the measured counts in the wings, the scaled first-order scatter provides a good approximation to the total scatter.

Third, the full singles spectrum 415 can be generated using an RTE method, as discussed in Y. Lu et al., "A deterministic integral spherical harmonics method for scatter simulation in computed tomography," Proc. SPIE 10132, Medical Imaging 2017: Physics of Medical Imaging, p. 101322H (2017), which is incorporated herein by reference in its entirety. Compared to MC methods, RTE can calculate first and multiple scatter events and does not suffer from statistical noise like in the MC method. The RTE method solves the problem $$\hat{\Omega} \cdot \nabla \psi(\vec{r}, E, \hat{\Omega}) + \lambda(\vec{r}, E, \hat{\Omega}) = \iint d\hat{\Omega}' dE' f(\vec{r}, E, E', \hat{\Omega} \cdot \hat{\Omega}') \psi(\vec{r}, E', \hat{\Omega}') + q(\vec{r}, E, \hat{\Omega})$$

wherein the boundary conditions are $$\psi(\vec{r}, E, \hat{\Omega}) = 0, \text{ for } \hat{n} \cdot \hat{\Omega} < 0 \text{ and}$$

$\psi(\vec{r}, E, \hat{\Omega})$ is the specific intensity of photon flux at point $\vec{r}$, at energy E, and in the direction of the solid angle $\hat{\Omega}$; q($\vec{r}, E, \hat{\psi}$) is emission map, $\hat{n}$ is the normal direction of the boundary surface; f($\vec{r}', E, E', \hat{\Omega} \cdot \hat{\Omega}'$) is the scatter cross section; $\mu(\vec{r}'', E)$ is the total attenuation coefficient of different tissue from $\mu$ map. In PET imaging, the scatter cross section f($\vec{r}', E, E', \hat{\Omega} \cdot \hat{\Omega}'$) can be limited to include only Compton scattering.

When the whole volume is discretized, each discretized region is evaluated as being a scatter source. The scatter map can be calculated iteratively to include successively higher orders of scatter, by using the expression $$\psi_s^k(\vec{r}, E, \hat{\Omega}) = \int_{\vec{r}_q}^{\vec{r}} d\vec{r}' \iint d\hat{\Omega}' dE' f(\vec{r}', E, E', \hat{\Omega} \cdot \hat{\Omega}') \times [$$
$$\psi_s^{k-1}(\vec{r}', E', \hat{\Omega}') + \psi_0(\vec{r}', E', \hat{\Omega}')] \exp\left[-\int_{\vec{r}'}^{\vec{r}} d\vec{r}'' \mu(\vec{r}'', E)\right]$$

wherein the superscript k denotes the highest order of scatter accounted for in a given iteration, and the contribution arising from first order scatter is given by $$\psi_0(\vec{r}, E, \hat{\Omega}) = q(\vec{r}_q, E, \hat{\Omega}') \delta(\hat{\Omega}' - \hat{\Omega}) \exp\left[-\int_{\vec{r}_q}^{\vec{r}} d\vec{r}'' \mu(\vec{r}'', E)\right].$$

For the first iteration in which k=1, $\psi_s^{k-1}(\vec{r}', E', \hat{\Omega}')$ is set to 0. The last iterations (i.e., the maximum value of $k_{MAX}$) can be reached when the desired precision is reached. For example, when the rate of convergence (e.g., the difference between $\psi_s^k$ and $\psi_s^{k-1}$) reaches a predetermined threshold. Given the scatter emission map $\psi_s^{k_{MAX}}$, the detector response $C_{SS_D}$ for the detector 540 at position $\vec{r}_D$ can be calculated as $$C_{SS_D}(\vec{r}_D, E) =$$
$$\iint d\hat{\Omega} \int_{\vec{r}_{sq}}^{\vec{r}_D} d\vec{r}' \iint d\hat{\Omega}' dE' f(\vec{r}', E, E', \hat{\Omega} \cdot \hat{\Omega}') \times \psi_s^{k_{MAX}}(\vec{r}', E', \hat{\Omega}')$$
$$\exp\left[-\int_{\vec{r}'}^{\vec{r}_D} d\vec{r}'' \mu(\vec{r}'', E)\right].$$

The detector response $C_{SS_D}$ provides the full singles spectrum. Additional details regarding how the above integrals can be approximated ad their computation can be accelerated using a spherical harmonic expansion are provided below.

Figure 7:
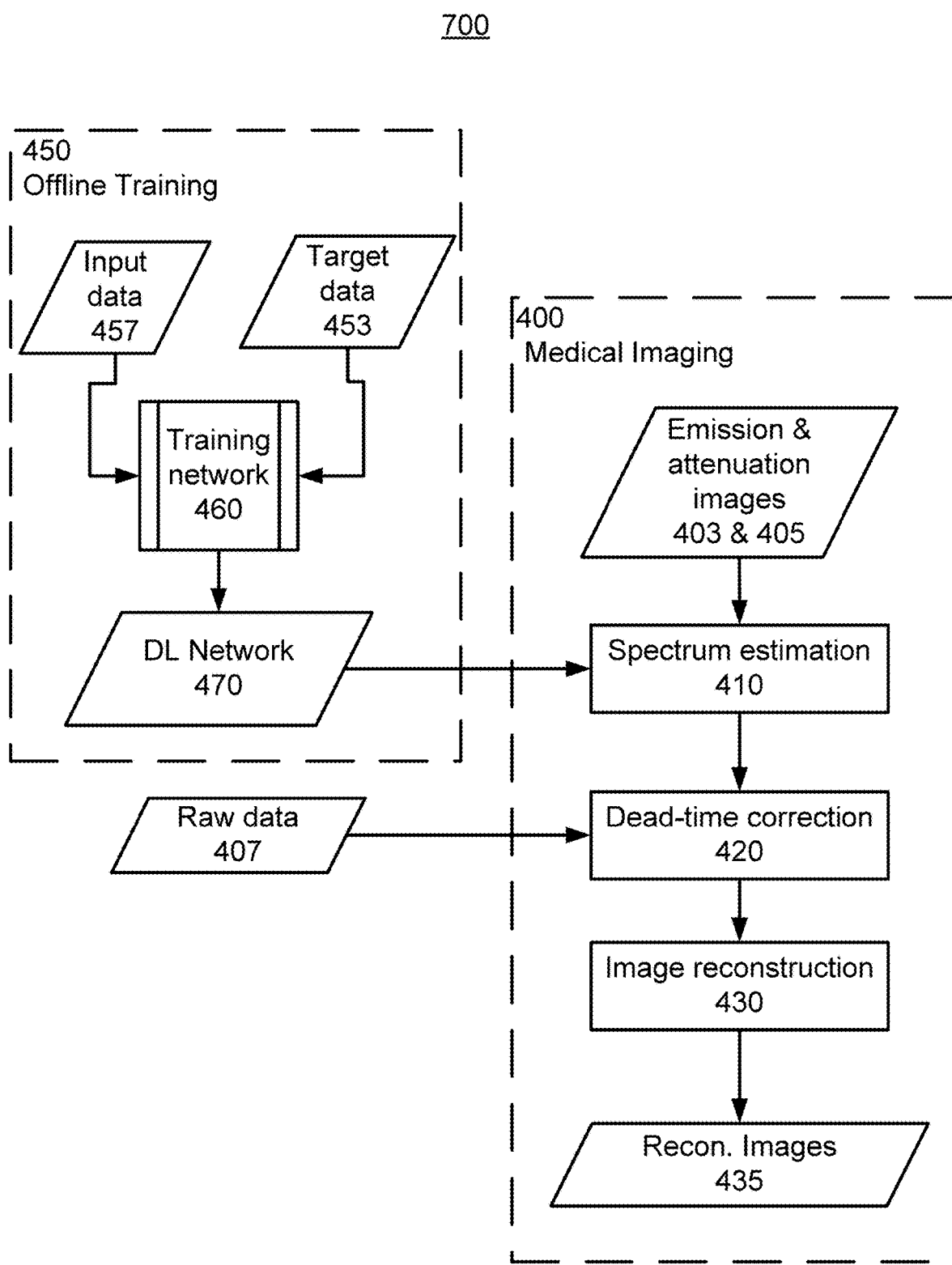
FIG. 7 shows a flow diagram of a method for estimating a full singles spectrum using a deep learning (DL) network, according to one implementation.

Fourth, the full singles spectrum 415 can be generated using a machine learning model such as an artificial neural network (ANN), also referred to herein a s deep learning (DL) network. DL networks can be trained using a training dataset to learn implicit patterns in the data that enable them to rapidly predict the full singles spectrum from the emission image 403 and the attenuation image 405. Even if training the DL network might take substantial time, training the DL network can occur only once, after which the trained DL network is used repeatedly for each image acquisition. Using the DL network to estimate the full singles spectrum FIG. 7 shows a flow diagram of a method 700 for PET imaging in which an emission image 403 and an attenuation image 405 are used to estimate a singles spectrum 415, and then use the singles spectrum 415 to correct raw data 407 that is then used to reconstruct a PET image 435.

Here, steps 410, 420, and 430 can be performed as discussed in reference to FIGS. 4A and 4B, except that step 410 receives as an input the DL network 470 and uses the network to estimate the singles spectrum 415. Further, FIG. 7 shows the raw data being an input to step 420, rather than step 410 as shown in FIG. 4A. Generally, step 410 can be performed without the raw data 407. In certain implementations, however, the raw data 407 can be used in step 410 (e.g., to determine a scaling factor when the analytical expression is used to calculate the scatter). Thus, implementations with and without the raw data 407 being used as an input at step 410 are contemplated as respective implementations of the disclosed method. Further, the raw data 407 can be used to generate the emission image 403 and the attenuation image 407 (e.g., using a joint-estimation method).

In process 460, input data 457 and target data 453 are used to train a DL network 470. The input data 457 includes pairs of emission images and the attenuation images that are applied as inputs to the DL network, and the target data 453 are full singles spectra that correspond to the respective pairs of emission and attenuation images in the input data 457. The target data 453 provide a gold standard to which the output of the DL network 470 are compared, such that the weighting coefficients between nodes of the network 470 can be adjusted (e.g., using a back propagation method) until the DL network 470 is fully trained to generate outputs that match the singles spectra of the target data 453. Additional details regarding how the DL network 470 is trained in process 460 are provided below.

Figure 8:
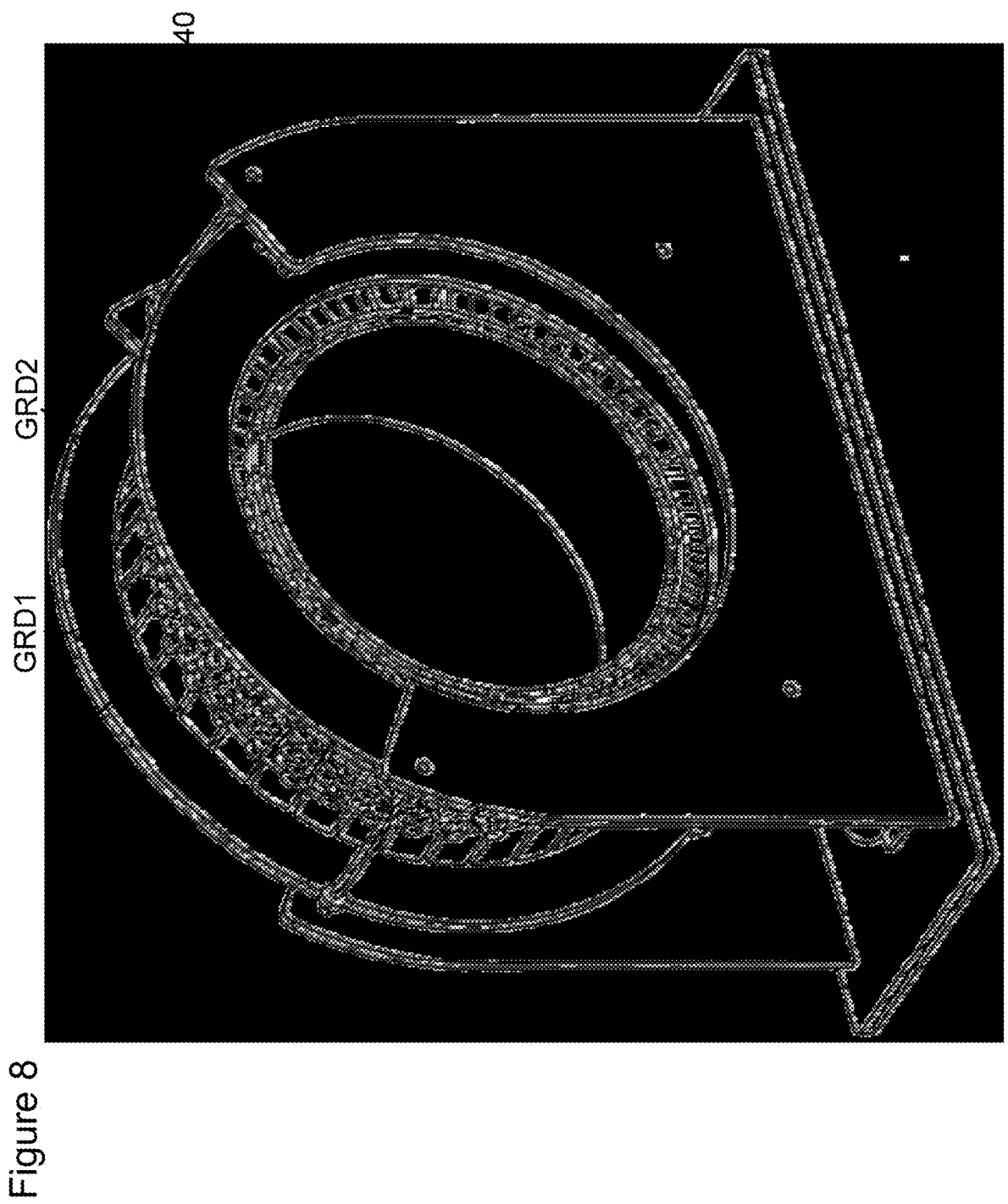
FIG. 8 shows a perspective view of a positron-emission tomography (PET) scanner, according to one implementation.
Figure 9:
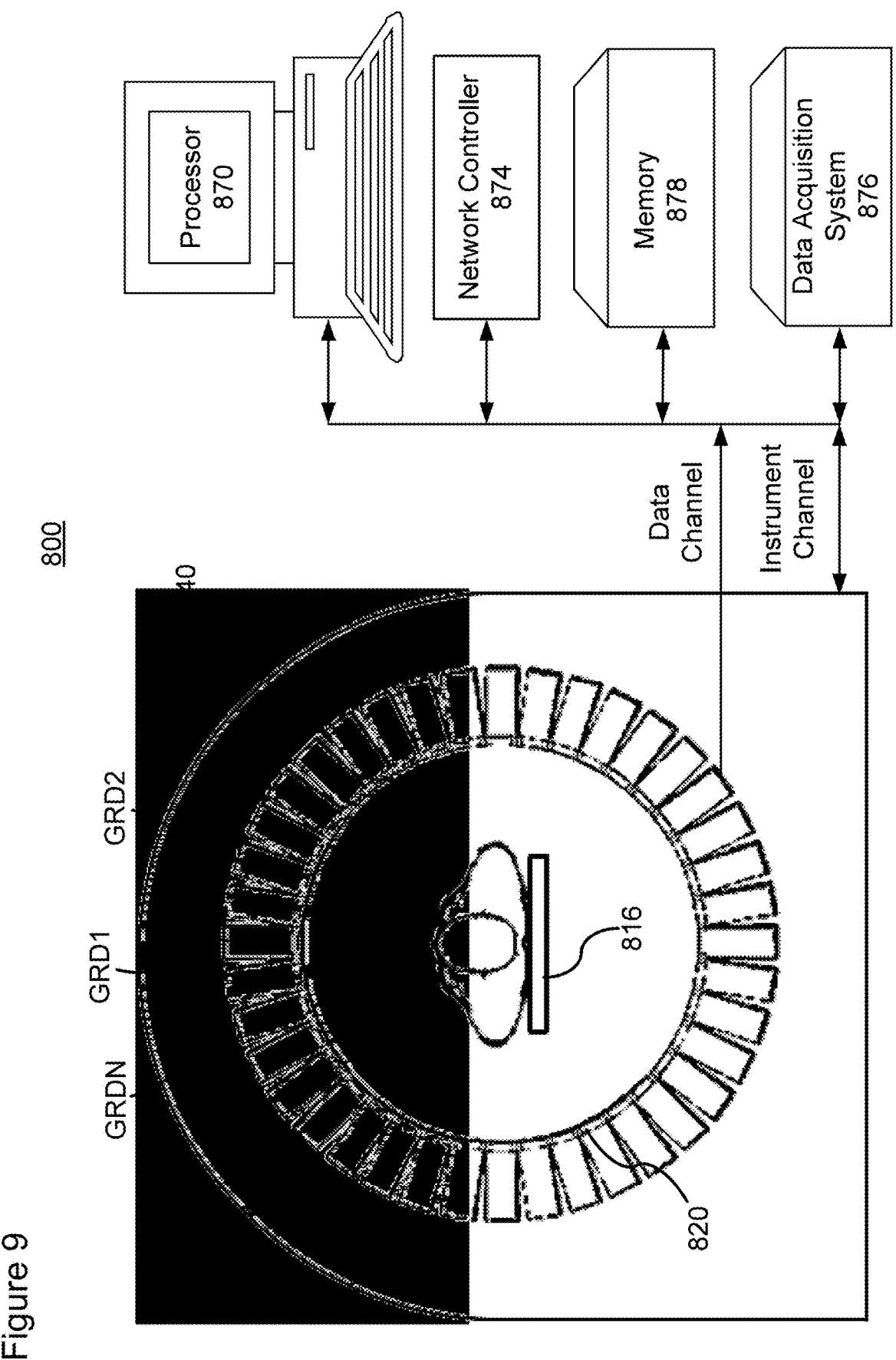
FIG. 9 shows a schematic view of the PET scanner, according to one implementation.

FIGS. 8 and 9 show a PET scanner 800 including a number of GRDs (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 800.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example.

FIG. 9 shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 8 and 9. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 9 shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 9, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data in accordance with methods 400 and 700, pre-reconstruction processing of the detection data, and post-reconstruction processing of the image data, as discussed herein.

The processor 870 can be configured to perform methods 400 and 700 described herein. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform methods 400 and 700 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed image can be displayed on a display. The display can be an LCD display, CRT display, plasma display, OLED, LED or any other display known in the art.

The memory 878 can be a hard disk drive, CD-ROM drive, DVD drive, FLASH drive, RAM, ROM or any other electronic storage known in the art.

The network controller 874, such as an Intel Ethernet PRO network interface card from Intel Corporation of America, can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 10:
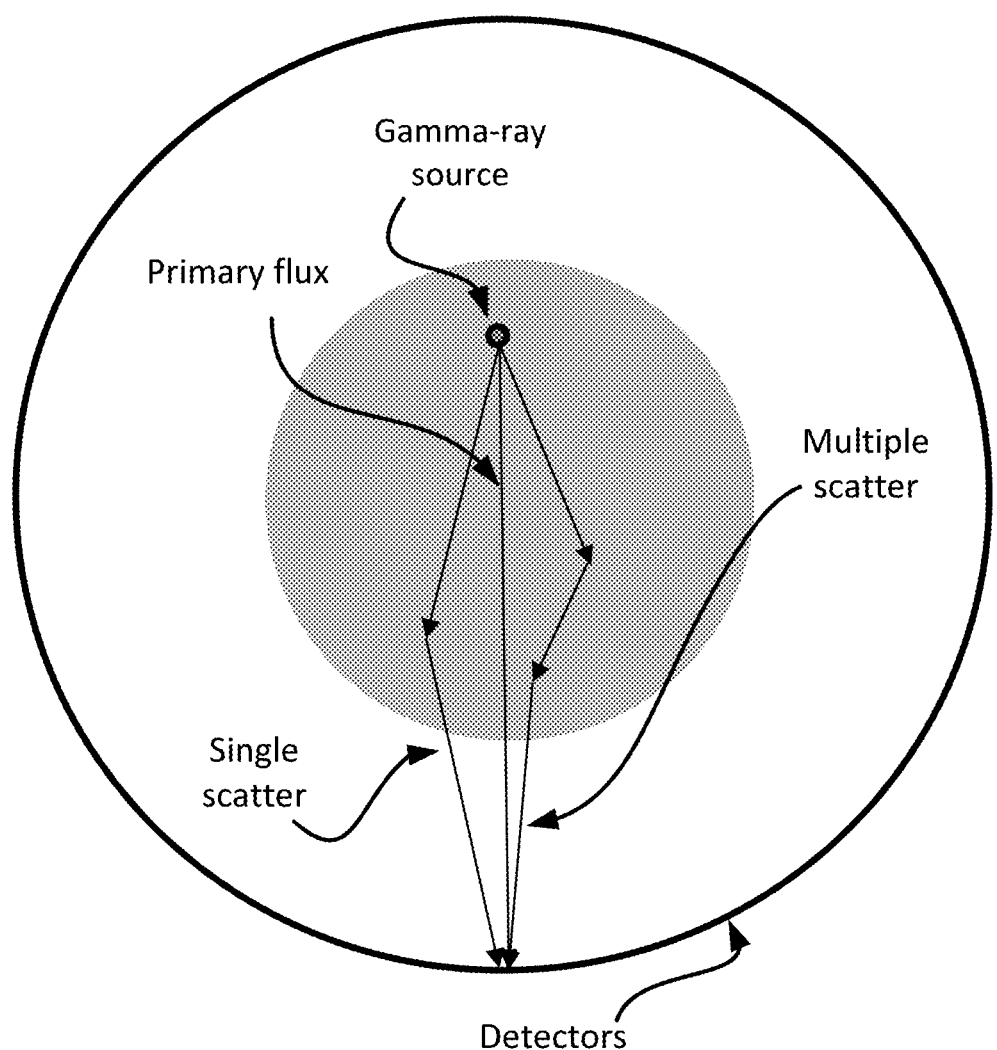
FIG. 10 shows a schematic diagram of primary flux, first-order scatter flux, and multi-scatter flux, according to one implementation.

Now a more detailed description of the RTE method is provided. FIG. 10 shows a diagram of the scatter process in which gamma-rays are emitted from a point denoted as the gamma-ray source, and three different processes are illustrated by which the gamma rays for the gamma-ray source arrive at a same detector within the ring of detectors: (i) a primary beam, (ii) first-order scatter, and (iii) multiple scatter. First, a primary flux is transmitted, with attenuation, through an object OBJ and detected at a given detector within the arrays of detectors. Second, the first-order scatter (denoted as the single scatter) occurs when the gamma ray is scatter just once before arriving at the detector. Third, multiple scatter (also referred to as higher-order scatter) occurs when the gamma ray is scatter multiple times before arriving at the detector. In certain implementations, the RTE method can be performed using three terms corresponding to the primary beam, first-order scatter, and multiple scatter.

Figure 11:
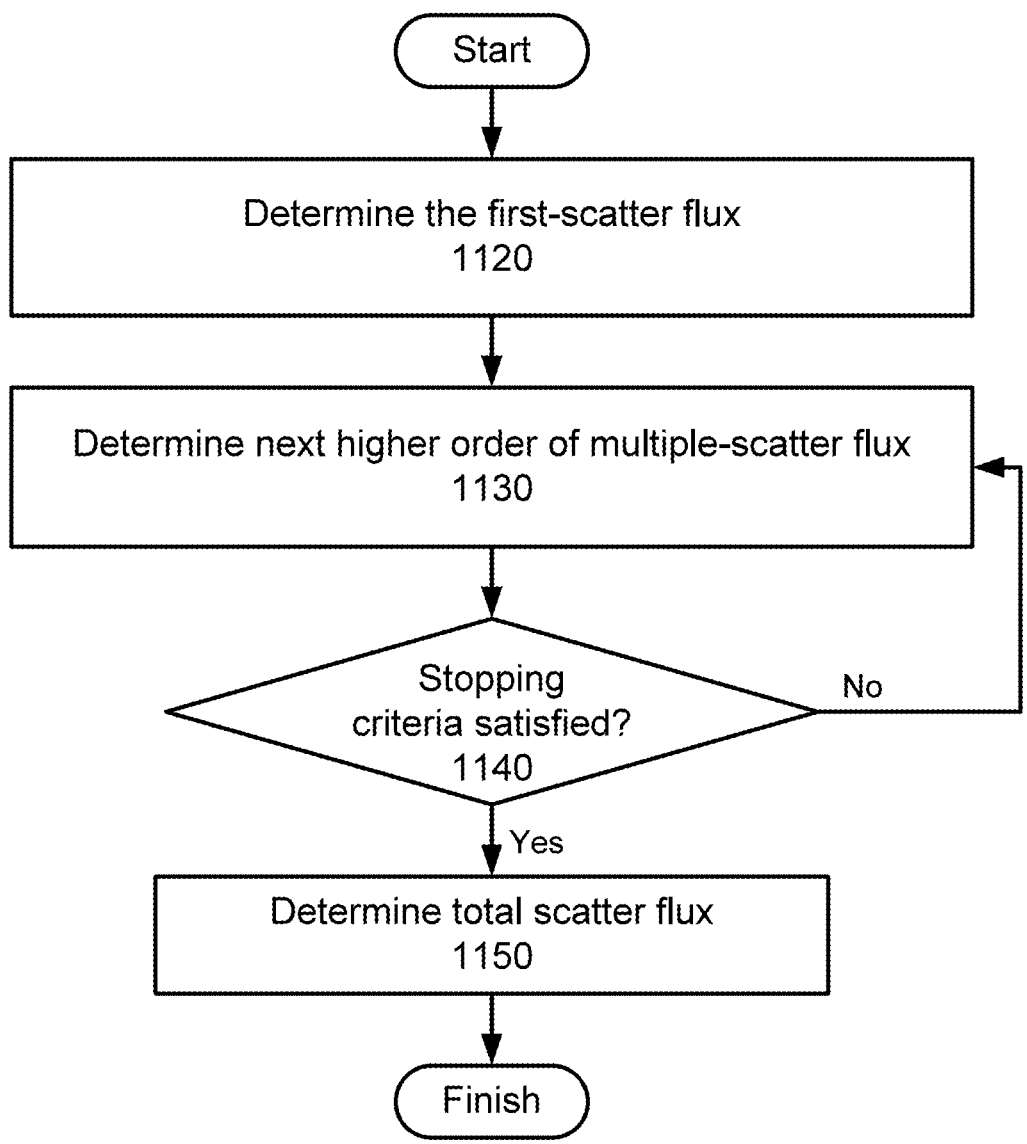
FIG. 11 shows a flow diagram of a process for performing a radiative transfer equation (RTE) method, according to one implementation.

FIG. 11 shows a flow diagram of a process 410 for simulating scatter using a three-step integral formulation of the RTE. Further, the process 410 is illustrated using a non-limiting embodiment in which a spherical harmonic expansion of the integrals is used to accelerate the calculations of the integrals, but process 410 is not limited to being performed using a spherical harmonic expansion. In certain implementations, for X-ray CT, the RTE scatter calculation using process 410 can account for both Compton and Rayleigh scattering, and, for PET, the RTE scatter calculation using process 410 can account for just Compton scattering.

The method described herein solves the above RTE by subdividing the RTE into three simpler integral problems in order to obtain precise, but straightforward scatter simulation for scatter estimation. This is achieved by first rewriting the RTE as the integral equation $$\psi(\vec{r}, E, \hat{\Omega}) = \psi_c(\vec{r}_c, E, \hat{\Omega}) \exp\left[\int_{\vec{r}_c}^{\vec{r}} d\vec{r}'' \mu(\vec{r}'', E)\right] +$$

$$\int_{\vec{r}_c}^{\vec{r}} d\vec{r}' \int\int d\hat{\Omega}' dE' f(\vec{r}', E, E', \hat{\Omega} \cdot \hat{\Omega}')$$

$$\psi(\vec{r}', E', \hat{\Omega}') \exp\left[-\int_{\vec{r}'}^{\vec{r}} d\vec{r}'' \mu(\vec{r}'', E')\right],$$

wherein the variable $\mu(\vec{r}, E)$ represents the attenuation coefficient at point $\vec{r}$ of X-rays having energy E.

As indicated in FIG. 10, the flux can be grouped into three components: (i) the primary flux, (ii) the first-scatter flux, and (iii) the multiple-scatter flux. Process 410 is organized to solve the integral equation representation of the RTE in steps corresponding to the above-identified three respective components of the flux. The RTE can be separated into at least two components (i.e., a scatter flux and a primary flux). Accordingly, given the primary flux $\psi_0(\vec{r}', E', \hat{\Omega}')$, the scatter flux $\psi_s(\vec{r}, E, \hat{\Omega})$ can be calculated by the integral expression $$\psi_s(\vec{r}, E, \hat{\Omega}) =$$

$$\int_{\vec{r}_c}^{\vec{r}} d\vec{r}' \int\int d\hat{\Omega}' dE' f(\vec{r}', E, E', \hat{\Omega} \cdot \hat{\Omega}') [\psi_s(\vec{r}', E', \hat{\Omega}') + \psi_0(\vec{r}', E', \hat{\Omega}')]$$

$$\exp\left[-\int_{\vec{r}'}^{\vec{r}} d\vec{r}'' \mu(\vec{r}'', E')\right],$$

as discussed above.

The integral equation for the scatter flux $\psi_s(\vec{r}, E, \hat{\Omega})$ can be further subdivided into a first scatter component $\psi_1(\vec{r}, E, l, m)$ and a multiple scatter component $\psi_s^k(\vec{r}, E, l, m)$ corresponding respectively to steps 1120 and 111230, which are described below.

In step 1120 of process 410, the first-scatter flux is calculated. The first-scatter flux can be calculated by a discretized integral formula, which is given by $$\psi_s^{k=1}(\vec{r}, E, l, m) = \int\int\int d^3\vec{r}' \exp\left[-\int_{\vec{r}'}^{\vec{r}} d\vec{r}'' \mu(\vec{r}'', E')\right] \frac{1}{|\vec{r} - \vec{r}'|^2} Y_{lm}^*(\hat{\Omega}) \times$$

$$\int dE' f(\vec{r}', E, E', \hat{\Omega} \cdot \hat{\Omega}') \psi_0(\vec{r}', E', \hat{\Omega}') \exp\left[-\int_{\vec{r}_c}^{\vec{r}} d\vec{r}'' \mu(\vec{r}'', E')\right],$$

wherein $Y^*_{lm}(\hat{\Omega})$ is the complex conjugation of a spherical harmonic function of degree l and order m, and $\psi_1(\vec{r}, E, lm)$ is the intensity of the first-scatter flux in the spherical-harmonics domain. The spherical harmonics can be given by $$Y_{lm}(\hat{\Omega}) = Y_{lm}(\theta, \phi) = N \exp(im\phi) P_l^m(\cos\theta),$$

wherein $Y_{lm}(\hat{\Omega})$ a spherical harmonic function of degree $\ell$ and order m, $P_l^m$ is an associated Legendre polynomial, N is a normalization constant, and $\theta$ and $\phi$ represent colatitude and longitude, respectively.

Different materials, such as bone and water, have different scattering cross-sections with different angular dependence depending on their atomic constituents. Also, the magnitude of the scatter cross-section can depend on the density of material components at the point $\vec{r}'$. Thus, the attenuation image 405 can be decomposed into material components to determine the density of various material components as a function of position to generate the position-dependent scatter cross-section.

In one non-limiting example, the material decomposition can be performed using dual-energy CT. Also, another option for the material decomposition is to use a threshold and region growing method that infers regions corresponding to material components by the attenuation of the voxels (e.g., voxels having a attenuation value above a predefined threshold in Hounsfield Units are determined to be bone).

In step 1130 of process 410, the higher-order scatter terms (i.e., multi scatter) are calculated. Whereas the first-scatter flux includes only X-ray photons that have been scattered one time, the $k^{th}$-order scatter term includes X-ray photons that have been scattered k times. After the first-scatter flux is calculated, the flux of multiple scatters can be calculated using a discretized integral spherical harmonics formula, which is given by $$\psi_s^k(\vec{r}, E, l, m) =$$

$$\psi_s^1(\vec{r}, E, l, m) + \int\int\int d^3\vec{r}' \exp\left[-\int_{\vec{r}'}^{\vec{r}} d\vec{r}'' \mu(\vec{r}'', E')\right] \frac{1}{|\vec{r}-\vec{r}'|^2} Y_{lm}^*(\hat{\Omega}) \times$$

$$\sum_{E'}\sum_{\bar{l}} f(\vec{r}', E, E', \bar{l}) \sum_m y_{\bar{l}m}(\hat{\Omega}) \psi_s^{k-1}(\vec{r}', E', \bar{l}, m),$$

wherein $\psi_s^k(\vec{r}, E, lm)$ and $\psi_s^{k-1}(\vec{r}', E', \overline{lm})$ are the intensity of the flux for multiple scatter including all scatter events up to order k and order k respectively and $f(\vec{r}', E, E', \bar{l})$ is the $\bar{l}$-th coefficient when the scatter cross-section is expanded using the Legendre polynomials. By defining the operator A as $$A = \int\int\int d^3\vec{r}' \exp\left[-\int_{\vec{r}'}^{\vec{r}} d\vec{r}'' \mu(\vec{r}'', E')\right]$$

$$\frac{1}{|\vec{r}-\vec{r}'|^2} Y_{lm}^*(\hat{\Omega}) \sum_{E'}\sum_{\bar{l}} f(\vec{r}', E, E', \bar{l}) \sum_m Y_{\bar{l}m}(\hat{\Omega}),$$

the above-defined iterative formula can be more simply expressed as $$\psi_s^{k+1} = A\psi_s^k + \psi_1.$$

In step 1140 of process 410, a stopping criteria is assessed to determine whether approximation up to order k is sufficiently accurate. That is, whether scattering accounted for by the above-defined iterative multiple-scatter calculation when calculated up to order k provides predefined stopping criteria, e.g., related to the accuracy requirements for the scatter correction of a given clinical application. In certain implementations, the stopping criteria can be satisfied when $$\frac{|\psi_s^{k+1} - \psi_s^k|}{\psi_s^k} \leq \delta t,$$

wherein ∂ is a predefined threshold. Further, the stopping criteria can be satisfied when a maximum value for k (i.e., a maximum number of iterations) has been reached. If the stopping criteria are satisfied, then process 410 proceeds from step 1140 to step 1150. Otherwise, step 1130 is repeated for the next higher order of multiple scattering.

In step 1150 of process 410, the flux at the detector is determined. After calculating the flux of multiple scatters, the above results can be combined to calculate the scatter flux intensity at the detector 540.

Now a more detailed description of training a DL network is provided (e.g., process 460). Here, the target data 453 are full singles spectra, which can be calculated, e.g., using an MC method or and RTE method. The input data are pairs of emission and attenuation images corresponding to the full singles spectra in the target data 453.

Figure 12:
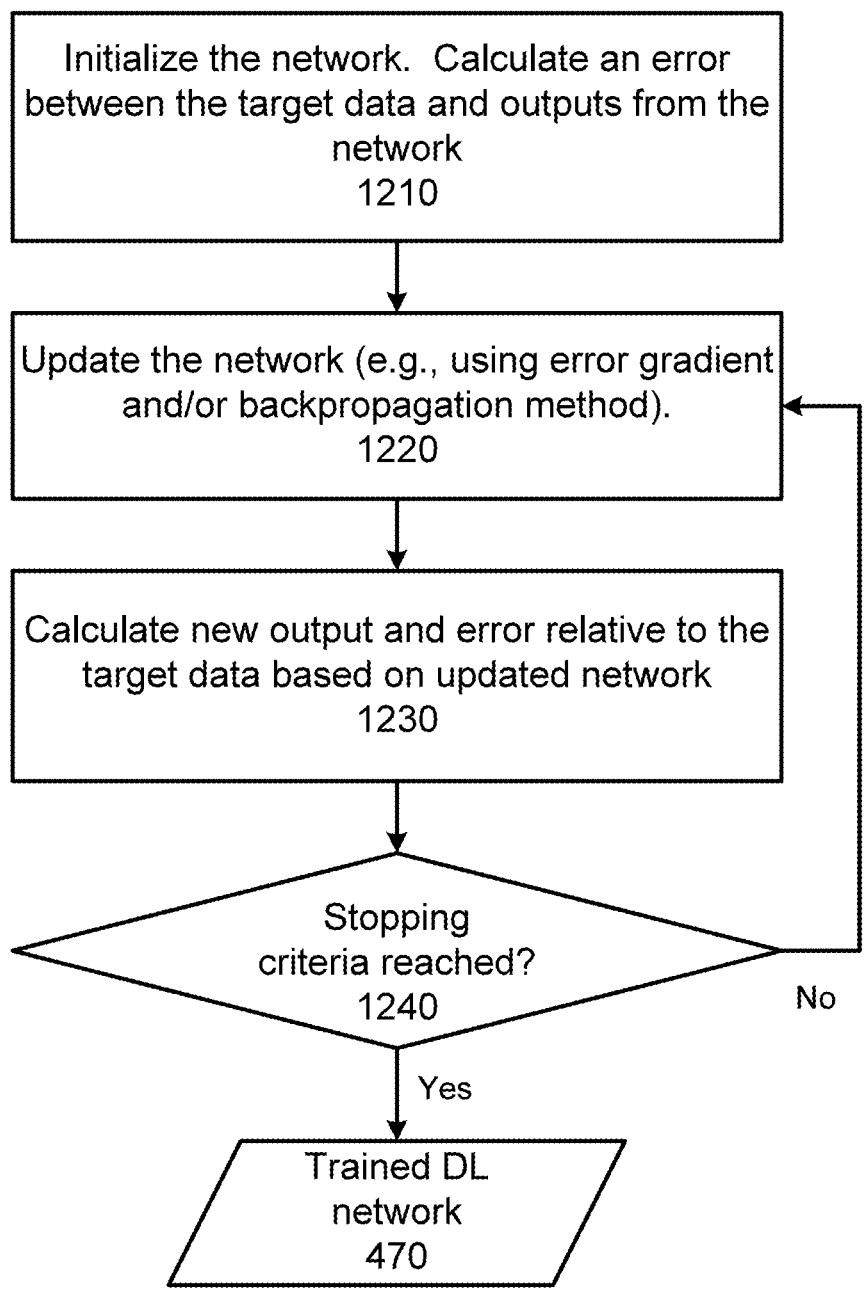
FIG. 12 shows a flow diagram for training a DL network to estimate the full singles spectrum, according to one implementation.

FIG. 12 shows a flow diagram of one implementation of the training process 460. In process 460, input data 457 and target data 453 are used as training data to train a DL network 470, resulting in the trained DL network 470 being output at step 1240. The offline DL training process 460 trains the DL network 470 using a training dataset in which respective emission and attenuation images of the input data 457 that are paired with corresponding full singles spectra of the target data 453 to train the DL network 470 to produce full singles spectra approximating those in the target data 453.

In process 460, a set of training data is obtained, and the network 470 is iteratively updated to reduce the error (e.g., the value produced by a loss function). The DL network infers the mapping implied by the training data, and the cost function produces an error value related to the mismatch between the target model parameters 453 and the result produced by applying a current incarnation of the DL network 470 to the input data 457. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a (stochastic) gradient descent method.

In step 1210 of process 460, an initial guess is generated for the coefficients of the DL network 470. Additionally, the initial guess can be based on one of a LeCun initialization, an Xavier initialization, and a Kaiming initialization.

Steps 1210 through 1240 of process 460 provide a non-limiting example of an optimization method for training the DL network 470.

An error is calculated (e.g., using a loss function or a cost function) to represent a measure of the difference (e.g., a distance measure) between the target data 453 and the output from the network generated by applying the input data 457 to a current version of the network 470. The error can be calculated using any known cost function or distance measure between the image data, including those cost functions described above. Further, in certain implementations the error/loss function can be calculated using one or more of a hinge loss and a cross-entropy loss. In certain implementations, the loss function can be the $\ell_p$-norm of the difference between the target data and the result of applying the input data to the DL network 470. Different values of "p" in the $\ell_p$-norm can be used to emphasize different aspects of the noise.

In certain implementations, the network 470 is trained using backpropagation. Backpropagation can be used for training neural networks and is used in conjunction with gradient descent optimization methods. During a forward pass, the algorithm computes the network's predictions based on the current parameters θ. These predictions are then input into the loss function, by which they are compared to the corresponding ground truth labels (i.e., the target data 453). During the backward pass, the model computes the gradient of the loss function with respect to the current parameters, after which the parameters are updated by taking a step of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 12, step 1220 of process 460 determines a change in the error as a function of the change in the network can be calculated (e.g., an error gradient), and this change in the error can be used to select a direction and step size for a subsequent change to the weights/coefficients of the DL network 470. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 1220 of process 460, a new set of coefficients are determined for the DL network 470. For example, the weights/coefficients can be updated using the changed calculated in step 1220, as in a gradient descent optimization method or an over-relaxation acceleration method.

In step 1230 of process 460, a new error value is calculated using the updated weights/coefficients of the DL network 470.

In step 1240, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 460 will continue back to the start of the iterative loop by returning and repeating step 1220 using the new weights and coefficients (the iterative loop includes steps 1220, 1230, and 1240). When the stopping criteria are satisfied the training process performed in process 460 is completed.

Figure 13:
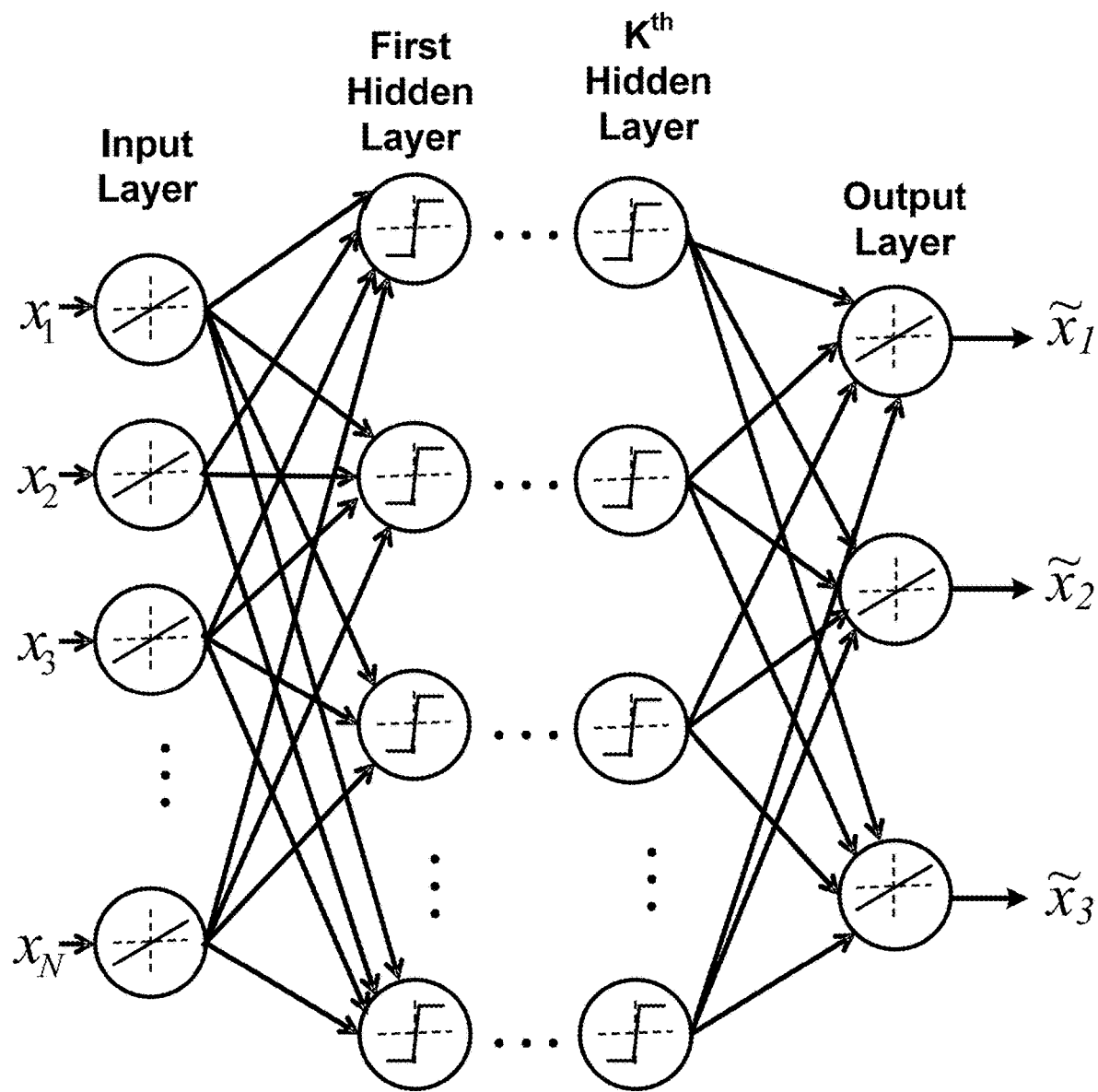
FIG. 13 shows a diagram of a DL network, according to one implementation.

FIG. 13 shows an example of the inter-connections between layers in the DL network 470. The DL network 470 can include fully connected, convolutional, and the pooling layer, all of which are explained below. In certain preferred implementations of the DL network 470, convolutional layers are placed close to the input layer, whereas fully connected layers, which perform the high-level reasoning, are place further down the architecture towards the loss function. Pooling layers can be inserted after convolutions and provide a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 470 can also incorporate batch normalization, as also exemplified in the first and second examples discussed above.

FIG. 13 shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m (x) is defined as a composition of other functions $n_i(x)$, which can further be defined as a composition of other functions. This can be conveniently represented as a network structure, with arrows depicting the dependencies between variables, as shown in FIG. 17. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 17, the neurons (i.e., nodes) are depicted by circles around a threshold function. For the non-limiting example shown in FIG. 17, the inputs are depicted as circles around a linear function, and the arrows indicate directed connections between neurons.

The above disclosure also encompasses the embodiments listed below.

(1) An apparatus that includes circuitry. The circuitry is configured to: (i) obtain radiation data representing an intensity of radiation detected at a plurality of detector elements, the radiation data comprising counts that have been filtered using an energy band-pass filter to generate filtered data, an energy range of the energy band-pass filter including an energy of the radiation when the radiation is not scattered, (ii) estimate, based on the radiation data, a singles spectrum of the radiation detected at a plurality of detector elements, the singles spectrum being estimated using a scatter model, and (iii) perform a dead-time correction correct on the radiation data based on the estimated singles spectrum, correcting the radiation data for missed detections arising from a dead time of respective detector elements of the plurality of detector elements to generate corrected radiation data.

(2) The apparatus according to (1), wherein the radiation detected at the plurality of detector elements comprises gamma rays, and the circuitry is further configured to obtain the radiation data by performing a positron emission tomography (PET) scan that generates the filtered data for which the energy range includes an energy of 511 keV, and reconstruct a PET image from the corrected radiation data.

(3) The apparatus according to (2), wherein the circuitry is further configured to obtain an emission image representing a density of gamma ray emitters as a function position within an object that is being imaged, and obtain an attenuation image representing attenuation as a function position within the object, determine, based on the attenuation image, a scatter cross section of the gamma rays as a function position within the object, and estimate the singles spectrum from the emission image and the determined scatter cross section.

(4) The apparatus according to (3), wherein the radiation data comprises X-ray computed tomography (CT) data and PET data, and the circuitry is further configured to (i) obtain the emission image by reconstructing a PET image from the PET data, and (ii) obtain the attenuation image by reconstructing a CT image from the X-ray CT data.

(5) The apparatus according to (3), wherein the radiation data comprises PET data, and the circuitry is further configured to obtain the emission image and the attenuation image using a joint-estimation PET method.

(6) The apparatus according to any of (1)-(5), wherein the circuitry is further configured to estimate the singles spectrum using a Monte Carlo method as the scatter model.

(7) The apparatus according to any of (1)-(6), wherein the circuitry is further configured to estimate the singles spectrum using an analytical expression as the scatter model, the analytical expression representing first-order scatter that is scaled to match tails of the radiation data.

(8) The apparatus according to any of (1)-(7), wherein the circuitry is further configured to estimate the singles spectrum using a radiative transfer equation (RTE) method as the scatter model.

(9) The apparatus according to any of (1)-(8), wherein, to perform the RTE method, the circuitry is further configured to integrate an attenuation of primary gamma-ray flux from an emission position of a gamma-ray emitter to a scatter position at which the gamma ray is scattered, determine a scatter flux at the scatter position by integrating scatter contributions from emission positions within the emission image, the scatter flux being a function of radiation energy and solid angle of the gamma ray after being scattered.

(10) The apparatus according to (9), wherein computation of the RTE is accelerated by the circuitry being further configured to calculate the scatter contributions from emission positions throughout the emission image using an approximation in which the scatter contributions are approximated using a predefined number of lowest terms of a spherical harmonic expansion.

(11) The apparatus according to any of (1)-(8), wherein the circuitry is further configured to estimate the singles spectrum using a neural network as the scatter model.

(12) The apparatus according to (11), wherein the neural network has been trained using a training dataset including input data and target data, the input data comprising pairs of attenuation images and emission images, and the target data comprising singles spectra that each correspond to a respective pair of an attenuation image and an emission image in the input data, the neural network being trained to generate an output that approximately matches a singles spectrum from the target data when the corresponding pair of the attenuation image and the emission image are applied as inputs to the neural network.

(13) The apparatus according to (11), wherein the circuitry is further configured to train the neural network by iteratively adjusting weighting coefficients of the neural network to optimize a value of a loss function, the loss function measuring a disagreement between respective singles spectra of target data and outputs from the neural network when the pairs of attenuation images and emission images corresponding to the respective singles spectra are applied to the neural network as inputs.

(14) A method that includes (i) obtaining radiation data representing an intensity of radiation detected at a plurality of detector elements, the radiation data comprising counts that have been filtered using an energy band-pass filter, an energy range of the energy band-pass filter including an energy of the radiation when the radiation is not scattered; (ii) estimating, based on the radiation data, a singles spectrum of the radiation detected at a plurality of detector elements, the singles spectrum being estimated using a scatter model; and (iii) performing, based on the estimated singles spectrum, a dead-time correction on the radiation data, the dead-time correction correcting the radiation data for missed detections arising from a dead time of respective detector elements of the plurality of detector elements to generate corrected radiation data.

(15) The method according to (14), wherein the radiation detected at the plurality of detector elements comprises gamma rays, the step of obtaining the radiation data further includes performing a positron emission tomography (PET) scan that generates the counts, which are filtered using the energy range that includes an energy of 511 keV, and the method further includes reconstructing a PET image from the corrected radiation data.

(16) The method according to (15) that further includes (i) obtaining an emission image representing a density of gamma ray emitters as a function position within an object that is being imaged, and obtain an attenuation image representing attenuation as a function position within the object, (ii) determining, based on the attenuation image, a scatter cross section of the gamma rays as a function position within the object, and (iii) estimating the singles spectrum from the emission image and the determined scatter cross section.

(17) The method according to (16), wherein the radiation data comprises X-ray computed tomography (CT) data and PET data, and the method further includes (i) obtaining the emission image by reconstructing a PET image from the PET data, and (ii) obtaining the attenuation image by reconstructing a CT image from the X-ray CT data.

(18) The method according to (16), wherein the radiation data comprises PET data, and the method further includes obtaining the emission image and the attenuation image using a joint-estimation PET method.

(19) The method according to any of (14)-(18), wherein the step of estimating the singles spectrum is performed using as the scatter model at least one of a Monte Carlo method, an analytical expression, a radiative transfer equation method, and a neural network, wherein the analytical expression represents first order single scatter that is scaled to match tails of the radiation data.

(20) The method according to any of (14)-(18), wherein the step of estimating the singles spectrum uses a radiative transfer equation (RTE) method as the scatter model, and the method further includes (i) integrating an attenuation of primary gamma-ray flux from an emission position of a gamma-ray emitter to a scatter position at which the gamma ray is scattered, and (ii) determining a scatter flux at the scatter position by integrating scatter contributions from emission positions within the emission image, the scatter flux being a function of radiation energy and solid angle of the gamma ray after being scattered.

(21) The method according to any of (20), wherein computing the RTE is accelerated by the circuitry being further configured to calculate the scatter contributions from emission positions throughout the emission image using an approximation in which the scatter contributions are approximated using a predefined number of lowest terms of a spherical harmonic expansion.

(22) The method according to any of (14)-(18), wherein the step of estimating the singles spectrum uses a neural network as the scatter model, and the neural network has been trained using a training dataset including input data and target data, the input data comprising pairs of attenuation images and emission images, and the target data comprising singles spectra that each correspond to a respective pair of an attenuation image and an emission image in the input data, the neural network being trained to generate an output that approximately matches a singles spectrum from the target data when the corresponding pair of the attenuation image and the emission image are applied as inputs to the neural network.

(23) The method according to any of (14)-(18), wherein the step of estimating the singles spectrum uses a neural network as the scatter model, and the method further includes training the neural network by iteratively adjusting weighting coefficients of the neural network to optimize a value of a loss function, the loss function measuring a disagreement between respective singles spectra of target data and outputs from the neural network when the pairs of attenuation images and emission images corresponding to the respective singles spectra are applied to the neural network as inputs.

(24) A non-transitory computer-readable storage medium including executable instructions, which when executed by circuitry, cause the circuitry to perform the method according to any of (14)-(23).

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

Obviously, numerous modifications and variations of the present invention are possible in light of the above teachings. It is therefore to be understood that within the scope of the appended claims, the invention may be practiced otherwise than as specifically described herein.

The invention claimed is:

1. An apparatus, comprising:
   circuitry configured to
   obtain radiation data representing an intensity of radiation detected at a plurality of detectors, the radiation data comprising counts that have been filtered using an energy band-pass filter, an energy range of the energy band-pass filter including an energy of the radiation when the radiation is not scattered,
   estimate, based on the radiation data, a singles spectrum of the radiation detected at a plurality of detectors, the singles spectrum being estimated using a scatter model, and
   perform, based on the estimated singles spectrum, a dead-time correction on the radiation data, the dead-time correction correcting the radiation data for missed detections arising from a dead time of respective detectors of the plurality of detectors to generate corrected radiation data.

2. The apparatus according to claim 1, wherein the radiation detected at the plurality of detectors comprises gamma rays, and
   the circuitry is further configured to
   obtain the radiation data by performing a positron emission tomography (PET) scan that generates the counts, which are filtered using the energy range that includes an energy of 511 keV, and
   reconstruct a PET image from the corrected radiation data.

3. The apparatus according to claim 2, wherein the circuitry is further configured to
   obtain an emission image representing a density of gamma ray emitters as a function position within an object that is being imaged, and obtain an attenuation image representing attenuation as a function position within the object,
   determine, based on the attenuation image, a scatter cross section of the gamma rays as a function position within the object, and
   estimate the singles spectrum from the emission image and the determined scatter cross section.

4. The apparatus according to claim 3, wherein
   the radiation data comprises X-ray computed tomography (CT) data and PET data, and
   the circuitry is further configured to
   obtain the emission image by reconstructing a PET image from the PET data, and
   obtain the attenuation image by reconstructing a CT image from the X-ray CT data.

5. The apparatus according to claim 3, wherein
   the radiation data comprises PET data, and
   the circuitry is further configured to obtain the emission image and the attenuation image using a joint-estimation PET method.

6. The apparatus according to claim 1, wherein the circuitry is further configured to estimate the singles spectrum using a Monte Carlo method as the scatter model.

7. The apparatus according to claim 1, wherein the circuitry is further configured to estimate the singles spectrum using an analytical expression as the scatter model, the analytical expression representing first-order scatter that is scaled to match tails of the radiation data.

8. The apparatus according to claim 1, wherein the circuitry is further configured to estimate the singles spectrum using a radiative transfer equation (RTE) method as the scatter model.

9. The apparatus according to claim 8, wherein, to perform the RTE method, the circuitry is further configured to
   integrate an attenuation of primary gamma-ray flux from an emission position of a gamma-ray emitter to a scatter position at which the gamma ray is scattered, and
   determine a scatter flux at the scatter position by integrating scatter contributions from emission positions within the emission image, the scatter flux being a function of radiation energy and solid angle of the gamma ray after being scattered.

10. The apparatus according to claim 9, wherein computation of the RTE is accelerated by the circuitry being further configured to calculate the scatter contributions from emission positions throughout the emission image using an approximation in which the scatter contributions are approximated using a predefined number of lowest terms of a spherical harmonic expansion.

11. The apparatus according to claim 1, wherein the circuitry is further configured to estimate the singles spectrum using a neural network as the scatter model.

12. The apparatus according to claim 11, wherein the neural network has been trained using a training dataset including input data and target data, the input data comprising pairs of attenuation images and emission images, and the target data comprising singles spectra that each correspond to a respective pair of an attenuation image and an emission image in the input data, the neural network being trained to generate an output that approximately matches a singles spectrum from the target data when the corresponding pair of the attenuation image and the emission image are applied as inputs to the neural network.

13. The apparatus according to claim 11, wherein the circuitry is further configured to train the neural network by iteratively adjusting weighting coefficients of the neural network to optimize a value of a loss function, the loss function measuring a disagreement between respective singles spectra of target data and outputs from the neural network when the pairs of attenuation images and emission images corresponding to the respective singles spectra are applied to the neural network as inputs.

14. A method, comprising:
obtaining radiation data representing an intensity of radiation detected at a plurality of detectors, the radiation data comprising counts that have been filtered using an energy band-pass filter, an energy range of the energy band-pass filter including an energy of the radiation when the radiation is not scattered;
estimating, based on the radiation data, a singles spectrum of the radiation detected at a plurality of detectors, the singles spectrum being estimated using a scatter model; and
performing, based on the estimated singles spectrum, a dead-time correction on the radiation data, the dead-time correction correcting the radiation data for missed detections arising from a dead time of respective detectors of the plurality of detectors to generate corrected radiation data.

15. The method according to claim 14, wherein
the radiation detected at the plurality of detectors comprises gamma rays,
the step of obtaining the radiation data further includes performing a positron emission tomography (PET) scan that generates the counts, which are filtered using the energy range that includes an energy of 511 keV, and
the method further includes reconstructing a PET image from the corrected radiation data.

16. The method according to claim 15, further comprising
obtaining an emission image representing a density of gamma ray emitters as a function position within an object that is being imaged, and obtain an attenuation image representing attenuation as a function position within the object,
determining, based on the attenuation image, a scatter cross section of the gamma rays as a function position within the object, and
estimating the singles spectrum from the emission image and the determined scatter cross section.

17. The method according to claim 16, wherein
the radiation data comprises X-ray computed tomography (CT) data and PET data, and
the method further comprises
obtaining the emission image by reconstructing a PET image from the PET data, and
obtaining the attenuation image by reconstructing a CT image from the X-ray CT data.

18. The method according to claim 16, wherein
the radiation data comprises PET data, and
the method further comprises obtaining the emission image and the attenuation image using a joint-estimation PET method.

19. A non-transitory computer-readable storage medium including executable instructions, which when executed by circuitry, cause the circuitry to perform the method according to claim 16.

20. The method according to claim 14, wherein
the step of estimating the singles spectrum is performed using as the scatter model at least one of a Monte Carlo method, an analytical expression, a radiative transfer equation method, and a neural network, wherein
the analytical expression represents first order single scatter that is scaled to match tails of the radiation data.

* * * * *